US008162842B2

(12) United States Patent
Gill et al.

(10) Patent No.: US 8,162,842 B2
(45) Date of Patent: Apr. 24, 2012

(54) DETECTING ISCHEMIA USING AN IMPLANTABLE CARDIAC DEVICE BASED ON MORPHOLOGY OF CARDIAC PRESSURE SIGNAL

(75) Inventors: Jong Gill, Valencia, CA (US); Peter Boileau, Valencia, CA (US); Gene A. Bornzin, Simi Valley, CA (US); Joseph J. Florio, Bend, OR (US); Xiaoyi Min, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 288 days.

(21) Appl. No.: 12/632,689

(22) Filed: Dec. 7, 2009

(65) Prior Publication Data

US 2010/0081952 A1    Apr. 1, 2010

Related U.S. Application Data

(62) Division of application No. 11/458,617, filed on Jul. 19, 2006, now Pat. No. 7,648,464.

(51) Int. Cl.
*A61B 5/04* (2006.01)
(52) U.S. Cl. ........................................ 600/508; 600/515
(58) Field of Classification Search .................. 600/508, 600/515
See application file for complete search history.

(56) References Cited

U.S. PATENT DOCUMENTS

| | | | |
|---|---|---|---|
| 4,686,988 A | 8/1987 | Sholder | |
| 4,708,142 A | 11/1987 | DeCote, Jr. | |
| 4,712,555 A | 12/1987 | Thornander et al. | |
| 4,729,376 A | 3/1988 | DeCote, Jr. | |
| 4,788,980 A | 12/1988 | Mann et al. | |
| 4,809,697 A | 3/1989 | Causey, III et al. | |
| 4,821,735 A * | 4/1989 | Goor et al. | 600/526 |
| 4,940,052 A | 7/1990 | Mann et al. | |
| 4,944,298 A | 7/1990 | Sholder | |
| 4,944,299 A | 7/1990 | Silvian | |
| 4,969,467 A | 11/1990 | Callaghan et al. | |
| 5,025,786 A | 6/1991 | Siegel | |
| 5,350,410 A | 9/1994 | Kleks et al. | |
| 5,676,690 A | 10/1997 | Noren | |
| 6,016,443 A | 1/2000 | Ekwall et al. | |
| 6,021,350 A | 2/2000 | Mathson | |
| 6,233,486 B1 | 5/2001 | Ekwall et al. | |
| 6,275,734 B1 | 8/2001 | McClure et al. | |
| 6,604,000 B2 | 8/2003 | Lu | |
| 6,609,023 B1 | 8/2003 | Fischell et al. | |
| 6,881,732 B2 * | 4/2005 | Winchell | 514/183 |
| 7,174,203 B2 | 2/2007 | Arand et al. | |
| 2003/0045805 A1 | 3/2003 | Sheldon et al. | |
| 2003/0158492 A1 | 8/2003 | Sheldon et al. | |

(Continued)

OTHER PUBLICATIONS

NonFinal Office Action, mailed Mar. 19, 2009: Related U.S. Appl. No. 11/458,599.

(Continued)

*Primary Examiner* — Eric D. Bertram

(57) ABSTRACT

Methods and systems are presented for using an ICD to detect myocardial ischemia. One such method includes sensing via an implantable cardiac-rhythm-management device (ICRMD) a signal indicative of cardiac pressure; determining via a processor associated with the ICRMD, a derivative signal that is a first derivative of the sensed signal; measuring via the processor, a maximum positive value of the derivative signal; measuring via the processor, a maximum negative value of the derivative signal; and indicating via the processor, an ischemia based on a comparison of a ratio of the maximum positive value to the maximum negative value with a predetermined value.

6 Claims, 17 Drawing Sheets

U.S. PATENT DOCUMENTS

2004/0167417 A1 8/2004 Schulhauser et al.
2007/0299356 A1 12/2007 Wariar et al.

OTHER PUBLICATIONS

Final Office Action, mailed Jun. 18, 2009: Related U.S. Appl. No. 11/458,599.

NonFinal Office Action, mailed May 28, 2009: Related U.S. Appl. No. 11/458,608.

Final Office Action, mailed Nov. 25, 2009: Related U.S. Appl. No. 11/458,608.

NonFinal Office Action, mailed Jan. 27, 2009: Related U.S. Appl. No. 11/458,617.

NonFinal Office Action, mailed Apr. 8, 2009: Related U.S. Appl. No. 11/458,617.

Notice of Allowance, mailed Nov. 18, 2009: Related U.S. Appl. No. 11/458,617.

* cited by examiner

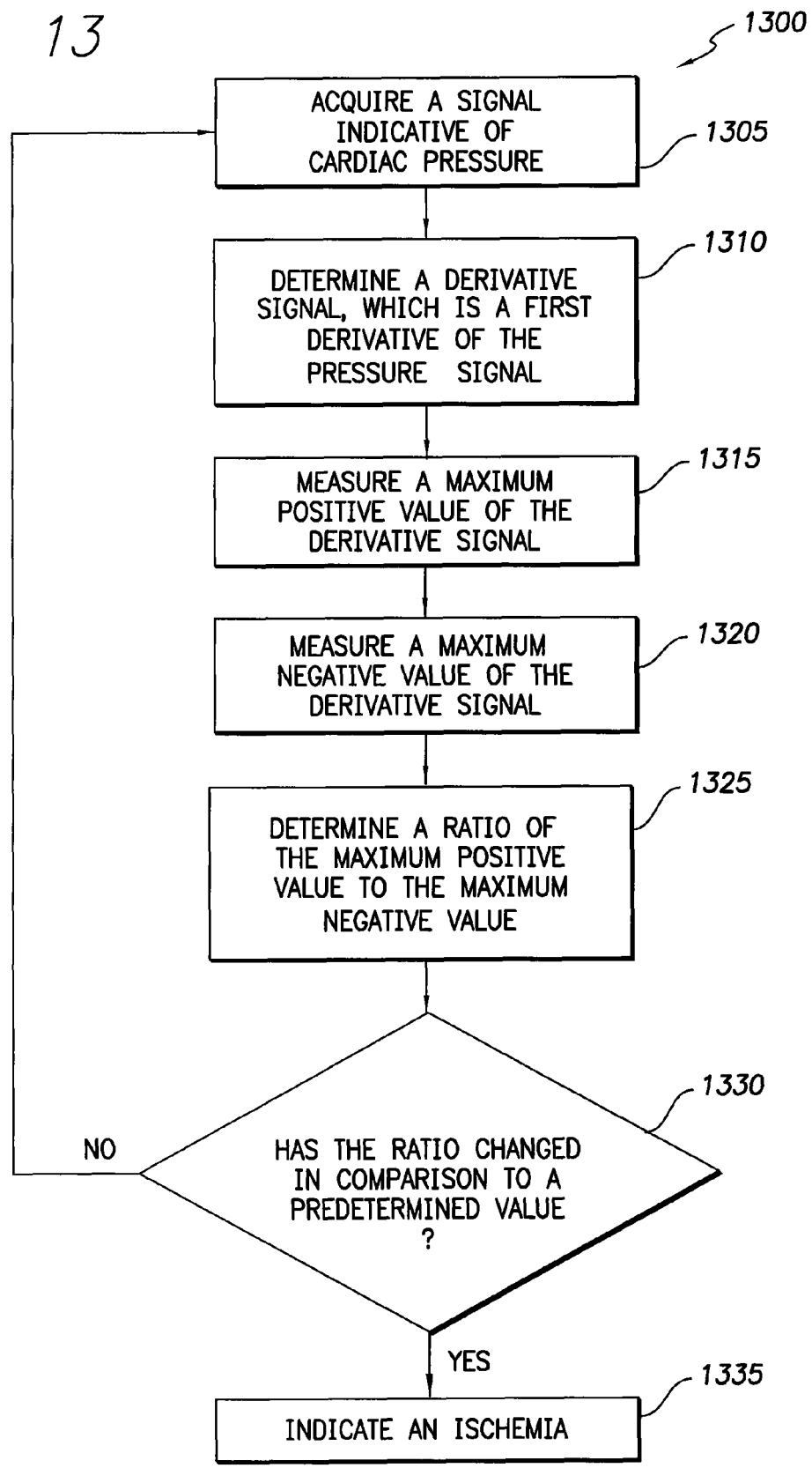

DETECTING ISCHEMIA USING AN IMPLANTABLE CARDIAC DEVICE BASED ON MORPHOLOGY OF CARDIAC PRESSURE SIGNAL

CROSS-REFERENCE TO RELATED APPLICATIONS

This application is a division of U.S. patent application Ser. No. 11/458,617, filed, Jul. 19, 2006, titled "Detecting Ischemia Using An Implantable Cardiac Device Based On Morphology Of Cardiac Pressure Signal", now U.S. Pat. No. 7,648,464, which is related to U.S. patent applications: 1) Ser. No. 11/458,599, titled "Detecting Ischemia Using An Implantable Cardiac Device Based On Analysis Of Delay In Cardiac Pressure Signal With Respect To Cardiac Electrical Signal", now abandoned; and 2) Ser. No. 11/458,608, titled "Detecting Ischemia Using An Implantable Cardiac Device Based On Correlation Of Cardiac Pressure Signal To Cardiac Electrical Signal", now abandoned.

FIELD OF THE INVENTION

The present invention relates generally to implantable cardiac devices and, more particularly, to methods and systems for detecting ischemia using an implantable cardiac device.

BACKGROUND ART

Myocardial ischemia is a cardiac function disorder caused by insufficient blood flow to the muscle tissue of the heart, most commonly due to narrowing of the coronary arteries. Conventional techniques monitor changes in an electrocardiogram (e.g., a surface electrocardiogram (ECG), or an internal electrogram (EGM) obtained by leads implanted in the heart) to detect myocardial ischemia. In particular, myocardial ischemia is typically diagnosed based on abnormalities detected in the ST segment of an electrocardiogram.

While monitoring cardiac electrical activity using an electrocardiogram is one technique for diagnosing myocardial ischemia, it is expected that cardiac pressure sensors of implantable cardiac devices will be used more frequently to monitor cardiac functionality. What is needed, therefore, are systems and methods for using an implantable cardiac device to monitor both electrical and mechanical conditions of the heart for reliable ischemia detection.

BRIEF SUMMARY

Methods and systems are presented for using an implantable cardiac device (ICD) to detect myocardial ischemia.

In a first exemplary embodiment, a method for detecting ischemia includes sensing a signal indicative of cardiac pressure, measuring a height of the sensed signal at a peak amplitude of the sensed signal, and measuring a duration of the sensed signal. The method further includes indicating an ischemia based on a comparison of a ratio of the height to the duration with a predetermined value.

In a second exemplary embodiment, a system for detecting ischemia includes an ischemia detector and a sensor that generates a signal indicative of cardiac pressure. The ischemia detector measures a height of the sensed signal at a peak amplitude of the sensed signal and measures a duration of the sensed signal. The ischemia detector indicates an ischemia based on a comparison of a ratio of the height to the duration with a predetermined value.

In a third exemplary embodiment, a method for detecting ischemia includes sensing a signal indicative of cardiac pressure and determining a derivative signal that is a first derivative of the sensed signal. The method also includes measuring a maximum positive value of the derivative signal and measuring a maximum negative value of the derivative signal. The method further includes indicating an ischemia based on a comparison of a ratio of the maximum positive value to the maximum negative value with a predetermined value.

In a fourth exemplary embodiment, a system for detecting ischemia includes an ischemia detector and a sensor that generates a signal indicative of cardiac pressure. The ischemia detector determines a derivative signal that is a first derivative of the sensed signal, measures a maximum positive value of the derivative signal, and measures a maximum negative value of the derivative signal. The ischemia detector indicates an ischemia based on a comparison of a ratio of the maximum positive value to the maximum negative value with a predetermined value.

Further features and advantages of the methods and systems presented herein, as well as the structure and operation of various example methods and systems, are described in detail below with reference to the accompanying drawings.

BRIEF DESCRIPTION OF THE DRAWINGS

The accompanying drawings, which are incorporated herein and form part of the specification, illustrate the methods and systems presented herein for using an ICRMD to detect myocardial ischemia. Together with the description, the drawings further serve to explain the principles of and to enable a person skilled in the relevant art(s) to make and use the methods and systems presented herein. In the drawings, like reference numbers indicate identical or functionally similar elements, and the drawing in which an element first appears is typically indicated by the leftmost digit(s) in the corresponding reference number.

FIG. 13 is a process flowchart providing example steps for detecting ischemia using an ICRMD to monitor characteristics of a derivative cardiac pressure signal.

DETAILED DESCRIPTION

Overview

The following detailed description of methods and systems for detecting ischemia using an ICRMD refers to the accompanying drawings that illustrate exemplary embodiments consistent with these methods and systems. Other embodiments are possible, and modifications may be made to the embodiments within the spirit and scope of the methods and systems presented herein. Therefore, the following detailed description is not meant to limit the methods and systems described herein. Rather, the scope of these methods and systems is defined by the appended claims.

It would be apparent to one of skill in the art that the methods and systems for detecting ischemia, as described below, may be implemented in many different embodiments of hardware, software, firmware, and/or the entities illustrated in the figures. Any actual software and/or hardware described herein is not limiting of these methods and systems. Thus, the operation and behavior of the methods and systems will be described with the understanding that modifications and variations of the embodiments are possible, given the level of detail presented herein.

Figure 1:
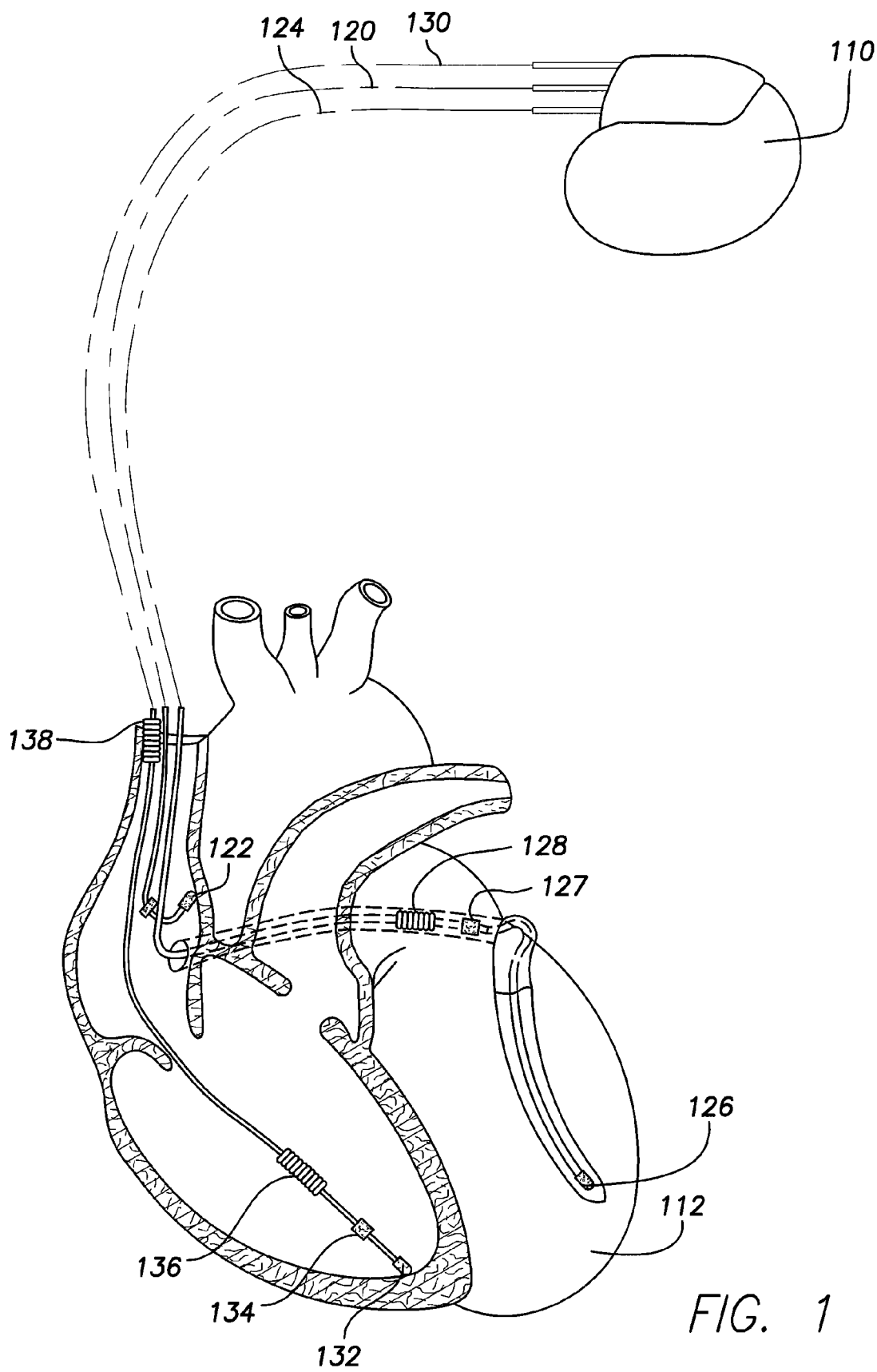
FIG. 1 is a simplified diagram illustrating an example ICRMD in electrical communication with a patient's heart by means of three leads suitable for delivering multi-chamber stimulation and pacing therapy.
Figure 2:
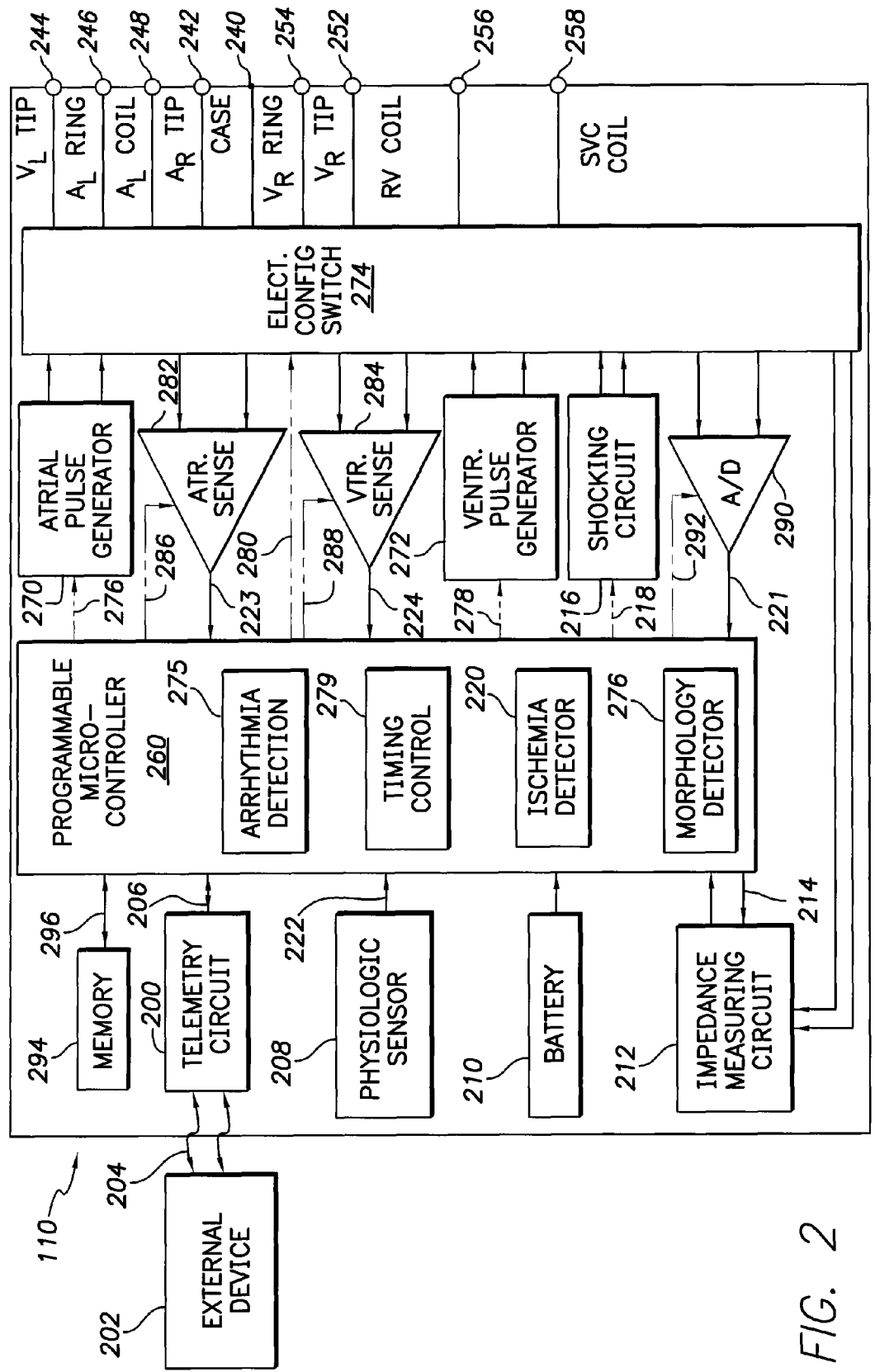
FIG. 2 is a functional block diagram of an example ICRMD that can provide cardioversion, defibrillation, and pacing stimulation in four chambers of a heart, in addition to ischemia detection.

Before describing the methods and systems for detecting ischemia in detail, it is helpful to describe an example environment in which these methods and systems may be implemented. The methods and systems described herein are particularly useful in the environment of an ICRMD. An ICRMD is a medical device that is implanted in a patient to monitor cardiac function and to deliver appropriate electrical therapy, for example, pacing pulses, cardioverting and defibrillator pulses, and drug therapy, as required. ICRMDs include, for example, pacemakers, cardioverters, defibrillators, implantable cardioverter defibrillators, implantable cardiac rhythm management devices, and the like. The term "implantable cardiac rhythm management device" or simply "ICRMD" is used herein to refer to any implantable cardiac device. FIGS. 1 and 2 illustrate such an environment including the methods and systems for detecting ischemia described herein.

Exemplary ICRMD in Electrical Communication with a Patient's Heart

FIG. 1 illustrates an exemplary ICRMD 110 in electrical communication with a patient's heart 112 by way of three leads, 120, 124 and 130, suitable for delivering multi-chamber stimulation and pacing therapy. To sense atrial cardiac signals and to provide right atrial chamber stimulation therapy, ICRMD 110 is coupled to implantable right atrial lead 120 having at least an atrial tip electrode 122, which typically is implanted in the patient's right atrial appendage.

To sense left atrial and ventricular cardiac signals and to provide left-chamber pacing therapy, ICRMD 110 is coupled to "coronary sinus" lead 124 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 124 is designed to receive atrial and ventricular cardiac signals and to deliver left ventricular pacing therapy using at least a left ventricular tip electrode 126, left atrial pacing therapy using at least a left atrial ring electrode 127, and shocking therapy using at least a left atrial coil electrode 128.

ICRMD 110 is also shown in electrical communication with the patient's heart 112 by way of implantable right ventricular lead 130 having, in this embodiment, a right ventricular tip electrode 132, a right ventricular ring electrode 134, a right ventricular (RV) coil electrode 136, and a superior vena cava (SVC) coil electrode 138. Typically, right ventricular lead 130 is transvenously inserted into heart 112 so as to place right ventricular tip electrode 132 in the right ventricular apex so that RV coil electrode 136 will be positioned in the right ventricle and SVC coil electrode 138 will be positioned in the SVC. Accordingly, right ventricular lead 130 is capable of receiving cardiac signals and delivering stimulation in the form of pacing and shock therapy to the right ventricle.

Functional Elements of an Exemplary ICRMD

FIG. 2 shows a simplified block diagram of ICRMD 110, which is capable of treating both fast and slow arrhythmias with stimulation therapy, including cardioversion, defibrillation, and pacing stimulation, and which is also capable of detecting myocardial ischemia. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 240 of ICRMD 110, shown schematically in FIG. 2, is often referred to as the "can," "case" or "case electrode" and may be programmably selected to act as the return electrode for all "unipolar" modes. Housing 240 may further be used as a return electrode for shocking purposes alone or in combination with one or more of coil electrodes, 128, 136, and 138, which are shown in FIG. 1. Housing 240 further includes a connector (not shown) having a plurality of terminals, 242, 244, 246, 248, 252, 254, 256, and 258 (shown schematically and, for convenience, the names of the electrodes to which they are connected are shown next to the terminals). As such, to achieve right atrial sensing and pacing, the connector includes at least a right atrial tip terminal (AR TIP) 242 adapted for connection to atrial tip electrode 122 (shown in FIG. 1).

To achieve left chamber sensing, pacing and shocking, the connector includes at least a left ventricular tip terminal (VL TIP) 244, a left atrial ring terminal (AL RING) 246, and a left atrial shocking terminal (AL COIL) 248, which are adapted for connection to left ventricular ring electrode 126, left atrial tip electrode 127, and left atrial coil electrode 128 (all shown in FIG. 1), respectively.

To support right chamber sensing, pacing, and shocking the connector also includes a right ventricular tip terminal (VR TIP) 252, a right ventricular ring terminal (VR RING) 254, a right ventricular shocking terminal (RV COIL) 256, and an SVC shocking terminal (SVC COIL) 258, which are configured for connection to right ventricular tip electrode 132, right ventricular ring electrode 134, RV coil electrode 136, and SVC coil electrode 138 (all shown in FIG. 1), respectively.

At the core of ICRMD 110 is a programmable microcontroller 260, which controls the various modes of stimulation therapy. As is well known in the art, microcontroller 260 typically includes a microprocessor, or equivalent control circuitry, designed specifically for controlling the delivery of stimulation therapy and can further include RAM or ROM memory, logic and timing circuitry, state machine circuitry, and I/O circuitry. Typically, microcontroller 260 includes the ability to process or monitor input signals (data) as controlled by a program code stored in a designated block of memory. The details of the design of microcontroller 260 are not critical to the techniques presented herein. Rather, any suitable microcontroller 260 can be used to carry out the functions described herein. The use of microprocessor-based control circuits for performing timing and data analysis functions are well known in the art.

Representative types of control circuitry that may be used with the techniques presented herein include the microprocessor-based control system of U.S. Pat. No. 4,940,052 (Mann et. al.) and the state-machines of U.S. Pat. No. 4,712,555 (Thornander et al.) and U.S. Pat. No. 4,944,298 (Sholder). For a more detailed description of the various timing intervals used within ICRMDs and their inter-relationship, see U.S. Pat. No. 4,788,980 (Mann et. al.). The '052, '555, '298 and '980 patents are incorporated herein by reference.

As shown in FIG. 2, an atrial pulse generator 270 and a ventricular pulse generator 272 generate pacing stimulation pulses for delivery by right atrial lead 120, right ventricular lead 130, and/or coronary sinus lead 124 (shown in FIG. 1) via an electrode configuration switch 274. It is understood that in order to provide stimulation therapy in each of the four chambers of the heart, atrial and ventricular pulse generators 270 and 272 may include dedicated, independent pulse generators, multiplexed pulse generators, or shared pulse generators. Pulse generators 270 and 272 are controlled by microcontroller 260 via appropriate control signals 276 and 278, respectively, to trigger or inhibit the stimulation pulses.

Microcontroller 260 further includes timing control circuitry 279, which is used to control pacing parameters (e.g., the timing of stimulation pulses) as well as to keep track of the timing of refractory periods, post ventricular atrial refractory period (PVARP) intervals, noise detection windows, evoked response windows, alert intervals, marker channel timing, etc., which are well known in the art. Examples of pacing parameters include, but are not limited to, atrio-ventricular (AV) delay, interventricular (RV-LV) delay, atrial interconduction (A-A) delay, ventricular interconduction (V-V) delay, and pacing rate. In an embodiment, microcontroller 260 analyzes a measured EGM signal to detect a desired interval of the EGM signal. For example, microcontroller 260 detects an R-wave of the EGM signal.

Switch 274 includes a plurality of switches for connecting the desired electrodes to the appropriate I/O circuits, thereby providing complete electrode programmability. Accordingly, switch 274, in response to a control signal 280 from microcontroller 260, determines the polarity of the stimulation pulses (e.g., unipolar, bipolar, combipolar, etc.) by selectively closing the appropriate combination of switches (not shown) as is known in the art.

Atrial sensing (ATR. SENSE) circuits 282 and ventricular sensing (VTR. SENSE) circuits 284 may also be selectively coupled to right atrial lead 120, coronary sinus lead 124, and right ventricular lead 130, which are shown in FIG. 1, through switch 274 for detecting the presence of cardiac activity in each of the four chambers of the heart. Accordingly, atrial and ventricular sensing circuits 282 and 284 may include dedicated sense amplifiers, multiplexed amplifiers, or shared amplifiers. In an embodiment, a dedicated sense amplifier directly senses an event such as an R-wave of a cardiac electrical activity signal. Switch 274 determines the "sensing polarity" of the cardiac signal by selectively closing the appropriate switches, as is also known in the art. In this way, a clinician may program the sensing polarity independent of the stimulation polarity.

Each sensing circuit, 282 and 284, preferably employs one or more low power, precision amplifiers with programmable gain and/or automatic gain control, bandpass filtering, and a threshold detection circuit, as known in the art, to selectively sense the cardiac signal of interest. The automatic gain control enables ICRMD 110 to deal effectively with the difficult problem of sensing the low amplitude signal characteristics of atrial or ventricular fibrillation. Such sensing circuits, 282 and 284, can be used to determine cardiac performance values used in the techniques presented herein.

The outputs of atrial and ventricular sensing circuits 282 and 284 are connected to microcontroller 260 which, in turn, are able to trigger or inhibit atrial and ventricular pulse generators, 270 and 272, respectively, in a demand fashion in response to the absence or presence of cardiac activity, in the appropriate chambers of the heart. Sensing circuits 282 and 284, in turn, receive control signals over signal lines 286 and 288 from microcontroller 260 for purposes of measuring cardiac performance at appropriate times, and for controlling the gain, threshold, polarization charge removal circuitry (not shown), and timing of any blocking circuitry (not shown) coupled to the inputs of sensing circuits 282 and 286.

For arrhythmia detection, ICRMD 110 utilizes the atrial and ventricular sensing circuits 282 and 284 to sense cardiac signals to determine whether a rhythm is physiologic or pathologic. The timing intervals between sensed events (e.g., P-waves, R-waves, and depolarization signals associated with fibrillation, which are sometimes referred to as "F-waves" or "Fib-waves") are then classified by microcontroller 260 by comparing them to a predefined rate zone limit (i.e., bradycardia, normal, low rate ventricular tachycardia (VT), high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Microcontroller 260 utilizes arrhythmia detection circuitry 275 and morphology detection circuitry 276 to recognize and classify arrhythmia so that appropriate therapy can be delivered.

In an embodiment, microcontroller 260 utilizes ischemia detector 220 for monitoring cardiac electrical activity and pressure data to diagnose myocardial ischemia. In one embodiment, ischemia detector 220 is implemented as hardware, firmware, software or a combination thereof within microcontroller 260.

Cardiac signals are also applied to the inputs of an analog-to-digital (A/D) data acquisition system 290. Data acquisition system 290 is configured to acquire electrical activity signals, such as EGM signals, convert the raw analog data into a digital signal, and store the digital signals for later processing and/or telemetric transmission to an external device 202. In FIG. 2, data acquisition system 290 is coupled to right atrial lead 120, coronary sinus lead 124, and right ventricular lead 130, which are shown in FIG. 1, through switch 274 to sample cardiac signals across any pair of desired electrodes. In another embodiment, data acquisition system 290 is coupled to receive electrical activity signals from subcutaneous dot electrodes distributed on housing 240 of ICRMD 110.

Advantageously, data acquisition system 290 can be coupled to microcontroller 260, or other detection circuitry, for detecting an evoked response from heart 112 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 260 detects a depolarization signal during a window following a stimulation pulse, the presence of which indicates that capture has occurred. Microcontroller 260 enables capture detection by triggering ventricular pulse generator 272 to generate a stimulation pulse, starting a capture detection window using timing control circuitry 279 within microcontroller 260, and enabling data acquisition system 290 via a control signal 292 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Kleks et. al.), which patents are hereby incorporated herein by reference. The type of capture detection system used is not critical to the techniques presented herein.

Microcontroller 260 is further coupled to a memory 294 by a suitable data/address bus 296. The programmable operating parameters used by microcontroller 260 are stored and modified, as required, in memory 294 in order to customize the operation of ICRMD 110 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to heart 112 within each respective tier of therapy.

Advantageously, the operating parameters of ICRMD 110 may be non-invasively programmed into memory 294 through a telemetry circuit 200 in telemetric communication with external device 202, such as a programmer, transtelephonic transceiver, or a diagnostic system analyzer. Telemetry circuit 200 is activated by microcontroller 260 by a control signal 206. Telemetry circuit 200 advantageously allows EGMs and status information relating to the operation of ICRMD 110 (as contained in microcontroller 260 or memory 294) to be sent to external device 202 through an established communication link 204. Telemetry circuit 200 also allows data obtained by an external sensor device to be passed to microcontroller 260 for analysis.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

ICRMD 110 further includes a physiologic sensor 208 that can be used to detect changes in cardiac performance or changes in the physiological condition of the heart. Accordingly, microcontroller 260 can respond by adjusting the various pacing parameters (such as rate, AV Delay, RV-LV Delay, V-V Delay, etc.). Microcontroller 260 controls adjustments of pacing parameters by, for example, controlling the stimulation pulses generated by the atrial and ventricular pulse generators 270 and 272. While shown as being included within ICRMD 110, it is to be understood that physiologic sensor 208 may also be external to ICRMD 110, yet still be implanted within or carried by the patient. More specifically, sensor 208 can be located inside ICRMD 110, on the surface of ICRMD 110, in a header of ICRMD 110, or on a lead (which can be placed inside or outside the bloodstream).

In an embodiment, physiologic sensor 208 can include an implantable, intra-ventricular pressure transducer that generates a signal indicative of ventricular cardiac pressure, characteristics of which can be monitored by ischemia detector 220 to diagnose myocardial ischemia. Physiologic sensor 208 is not limited to pressure transducers, and can include other types of sensors capable of generating a signal indicative of ventricular cardiac pressure, such as strain gauge sensors, photoplethysmography (PPG) sensors, and the like.

ICRMD 110 further includes a magnet detection circuitry (not shown), coupled to microcontroller 260. It is the purpose of the magnet detection circuitry to detect when a magnet is placed over ICRMD 110. A clinician may use the magnet to perform various test functions of ICRMD 110 and/or to signal microcontroller 260 that external device 202 is in place to receive or transmit data to microcontroller 260 through telemetry circuit 200.

As further shown in FIG. 2, ICRMD 110 is shown as having an impedance measuring circuit 212, which is enabled by microcontroller 260 via a control signal 214. The known uses for an impedance measuring circuit 212 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. Impedance measuring circuit 212 is advantageously coupled to switch 274 so that any desired electrode may be used. Impedance measuring circuit 212 is not critical to the techniques presented herein and is shown only for completeness.

In the case where ICRMD 110 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 260 further controls a shocking circuit 216 by way of a control signal 218. Shocking circuit 216 generates shocking pulses of low (e.g., up to 0.5 Joules), moderate (e.g., 0.5-10 Joules), or high energy (e.g., 11-40 Joules), as controlled by microcontroller 260. Such shocking pulses are applied to the patient's heart 112 through at least two shocking electrodes (e.g., selected from left atrial coil electrode 128, RV coil electrode 136, and SVC coil electrode 138, which are shown in FIG. 1). As noted above, housing 240 may act as an active electrode in combination with RV electrode 136, or as part of a split electrical vector using SVC coil electrode 138 or left atrial coil electrode 128 (i.e., using the RV electrode as a common electrode).

Cardioversion shocks are generally considered to be of low to moderate energy level (so as to minimize pain felt by the patient), and/or synchronized with an R-wave, and/or pertaining to the treatment of tachycardia. Defibrillation shocks are generally of moderate to high energy level (i.e., corresponding to thresholds in the range of about 5-40 Joules), delivered asynchronously (since R-waves may be too disorganized to be recognized), and pertaining exclusively to the treatment of fibrillation. Accordingly, microcontroller 260 is capable of controlling the synchronous or asynchronous delivery of the shocking pulses.

ICRMD 110 additionally includes a battery 210, which provides operating power to a load that includes all of the circuits shown in FIG. 2.

Methods and Systems for Detecting Myocardial Ischemia Using an ICRMD

Example methods and systems for detecting myocardial ischemia using an ICRMD are described below. These methods and systems diagnose myocardial ischemia based on a cardiac pressure signal.

In a first embodiment, ischemia is diagnosed based on correlation of a cardiac electrical activity signal to the cardiac pressure signal. For example, ischemia is indicated when an average value or a peak value of the cardiac pressure signal corresponding in time to a detectable feature of the cardiac electrical signal is attenuated (i.e., decreases in amplitude) over a predetermined interval. In this case, the cardiac pressure signal is normalized using a baseline value and is referenced to a reference signal/value.

In a second embodiment, ischemia is diagnosed based on correlation of the cardiac electrical activity signal to a derivative cardiac pressure signal, which is a first derivative of the cardiac pressure signal. For example, ischemia is indicated when a peak value of the derivative cardiac pressure signal is attenuated over a predetermined interval.

In a third embodiment, ischemia is indicated based on analysis of a delay in the cardiac pressure signal with respect to the cardiac electrical activity signal. For example, the delay is measured from an R-wave of the cardiac electrical activity signal to a peak value of the cardiac pressure signal.

In a fourth embodiment, ischemia is indicated based on analysis of a delay in the derivative cardiac pressure signal with respect to the cardiac electrical activity signal. For example, the delay is measured from an R-wave of the cardiac electrical activity signal to a peak value of the derivative cardiac pressure signal.

In a fifth embodiment, ischemia is diagnosed based on morphology of the cardiac pressure signal. For example, ischemia is indicated based on analysis of a ratio of an amplitude (i.e., height) of the cardiac pressure signal to a duration (i.e., width) of the cardiac pressure signal.

In a sixth embodiment, ischemia is diagnosed based on morphology of the derivative cardiac pressure signal. For example, ischemia is indicated based on analysis of a ratio of a maximum value of a positive (i.e., rising) portion of the derivative cardiac pressure signal to a maximum value of a negative (i.e., falling) portion of the derivative cardiac pressure signal. These example methods and systems are described below in more detail.

An example system for detecting myocardial ischemia is shown in FIG. 2, which is described above in detail. FIG. 2 illustrates ICRMD 110, which includes, among other elements, microcontroller 260, ischemia detector 220, data acquisition system 290, atrial and ventricular sensing circuits 282 and 284, and physiologic sensor 208. In an embodiment, ischemia detector 220 monitors cardiac electrical activity events obtained by data acquisition system 290 and atrial and ventricular sensing circuits 282 and 284 and cardiac ventricular pressure data obtained by physiologic sensor 208 to diagnose myocardial ischemia.

As described above, cardiac signals are applied to the inputs of data acquisition system 290, which can be configured to acquire signals indicative of cardiac electrical activity (e.g., internal EGM signals, cardiac electrical activity signals obtained from subcutaneous dot electrodes, etc.). Alternatively, or in addition to data acquisition system 290, atrial and ventricular sensing circuits 282 and 284 can include dedicated sense amplifiers to directly sense cardiac electrical activity signal events (e.g., an R-wave, etc.). Additionally, physiologic sensor 208 can be configured to acquire signals indicative of ventricular cardiac pressure. For example, physiologic sensor 208 can include an implantable, intraventricular pressure transducer desirably positioned in the left ventricle (but can also be positioned in the right ventricle). Alternatively, or in addition to a pressure transducer, physiologic sensor 208 can include other sensors capable of generating a signal indicative of ventricular cardiac pressure, such as strain gauge sensors, PPG sensors, and the like.

As shown in FIG. 2, an output signal 221 from data acquisition system 290, output signals 223 and 224 from atrial and ventricular sensing circuits 282 and 284, and an output signal 222 from physiologic sensor 208 are coupled to microcontroller 260, enabling ischemia detector 220 to monitor various cardiac pressure signal characteristics to detect ischemia.

Several example techniques for monitoring a cardiac pressure signal to detect ischemia are described below. First, example techniques are described for correlating amplitude of the cardiac pressure signal to cardiac electrical activity signal events to detect ischemia. Next, example techniques are described for analyzing delay of the cardiac pressure signal with respect to cardiac electrical activity signal events to detect ischemia. Finally, example techniques are described for analyzing cardiac pressure signal morphology to detect ischemia.

Correlation of Cardiac Pressure Signal to Cardiac Electrical Signal

In this section, example techniques are described for correlating amplitude of a cardiac pressure signal to cardiac electrical activity signal events to detect ischemia. In a first example, ischemia detector 220 indicates an ischemia when an average value or a peak value of a signal indicative of ventricular cardiac pressure is attenuated over a predetermined interval of a signal indicative of cardiac electrical activity. In a second example, ischemia detector 220 indicates an ischemia when a peak value of a derivative signal, which is a first derivative of a signal indicative of ventricular cardiac pressure, is attenuated over a predetermined interval of a signal indicative of cardiac electrical activity.

Figure 3:
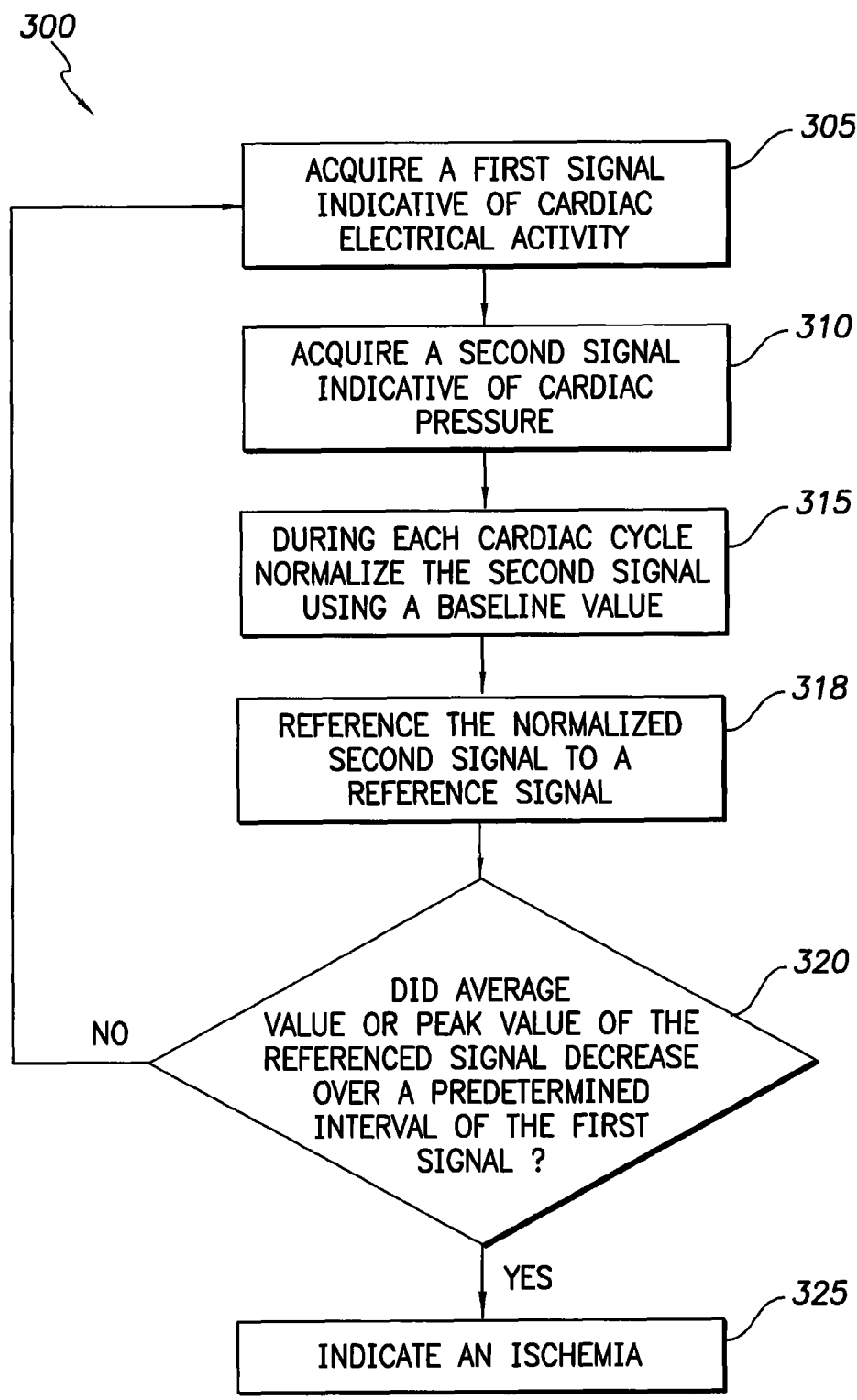
FIG. 3 is a process flowchart providing example steps for detecting ischemia using an ICRMD to monitor characteristics of a cardiac pressure signal.
Figure 6:
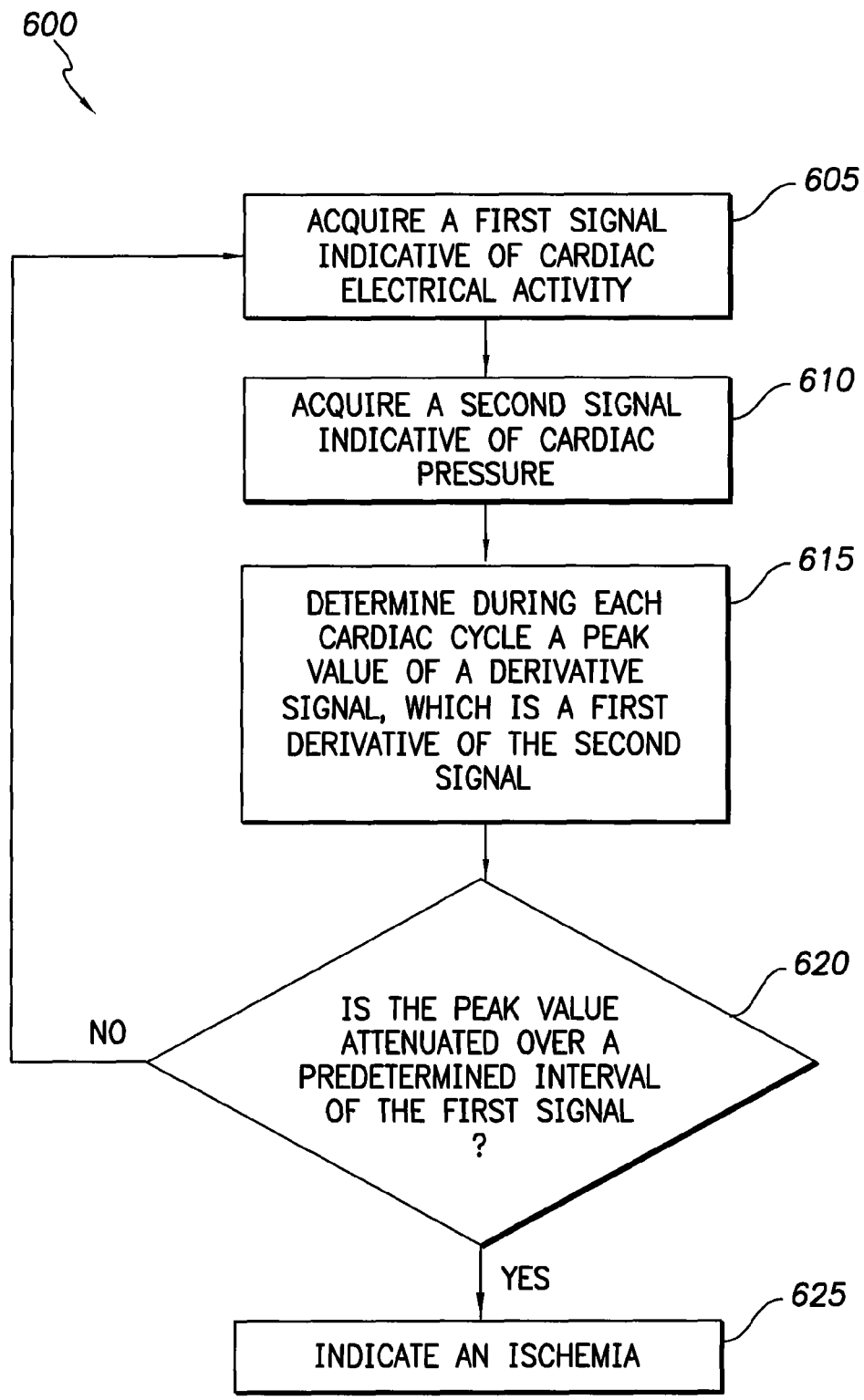
FIG. 6 is a process flowchart providing example steps for detecting ischemia using an ICRMD to monitor characteristics of a derivative cardiac pressure signal.

FIGS. 3 and 6 show process flowcharts providing example steps for detecting myocardial ischemia using an ICRMD. The steps of FIGS. 3 and 6 do not necessarily have to occur in the order shown, as will be apparent to persons skilled in the relevant art(s) based on the teachings herein. Other operational and structural embodiments will be apparent to persons skilled in the relevant art(s) based on the following discussion. These steps are described in detail below.

FIG. 3 shows a process flowchart 300 providing steps for detecting ischemia using an ICRMD. In step 305, a first signal indicative of cardiac electrical activity is acquired. For example, as described above with respect to FIG. 2, data acquisition system 290 is configured to acquire cardiac electrical activity data and provide an output signal 221 indicative of cardiac electrical activity to ischemia detector 220. Alternatively, or in addition to data acquisition system 290, atrial and ventricular sensing circuits 282 and 284 can include dedicated sense amplifiers to directly sense cardiac electrical activity signal events (e.g., an R-wave, etc.) and provide output signals 223 and 224 indicative of cardiac electrical activity to ischemia detector 220. An exemplary first electrical signal is the intracardiac electrogram (IEGM) obtained from right ventricular tip 132 to a can 110 in FIG. 1. Various other unipolar and bipolar configurations can be used as well.

In step 310, a second signal indicative of cardiac pressure is acquired. For example, as described above with respect to FIG. 2, physiologic sensor 208 can be configured to acquire ventricular cardiac pressure data via a pressure transducer or other type of sensor and provide an output signal 222 indicative of ventricular cardiac pressure to ischemia detector 220.

The second signal can be measured on an ensemble-average of several (e.g., 8-16) consecutive or approximately consecutive cardiac pressure signal measurements. Alternatively, the second signal can be measured for each of several individual consecutive or approximately consecutive cardiac pressure signal measurements, and a statistical measurement, such as the mean and the variance, can be calculated on the several measurements.

In step 315, the second signal is normalized using a baseline value (e.g. an isobaric baseline value is subtracted). The baseline value is a value of the second signal corresponding in time to a detectable feature of the first signal. In an embodiment, the baseline value is the value of the second signal corresponding in time to a peak of the first signal (e.g. an R-wave).

Figure 4:
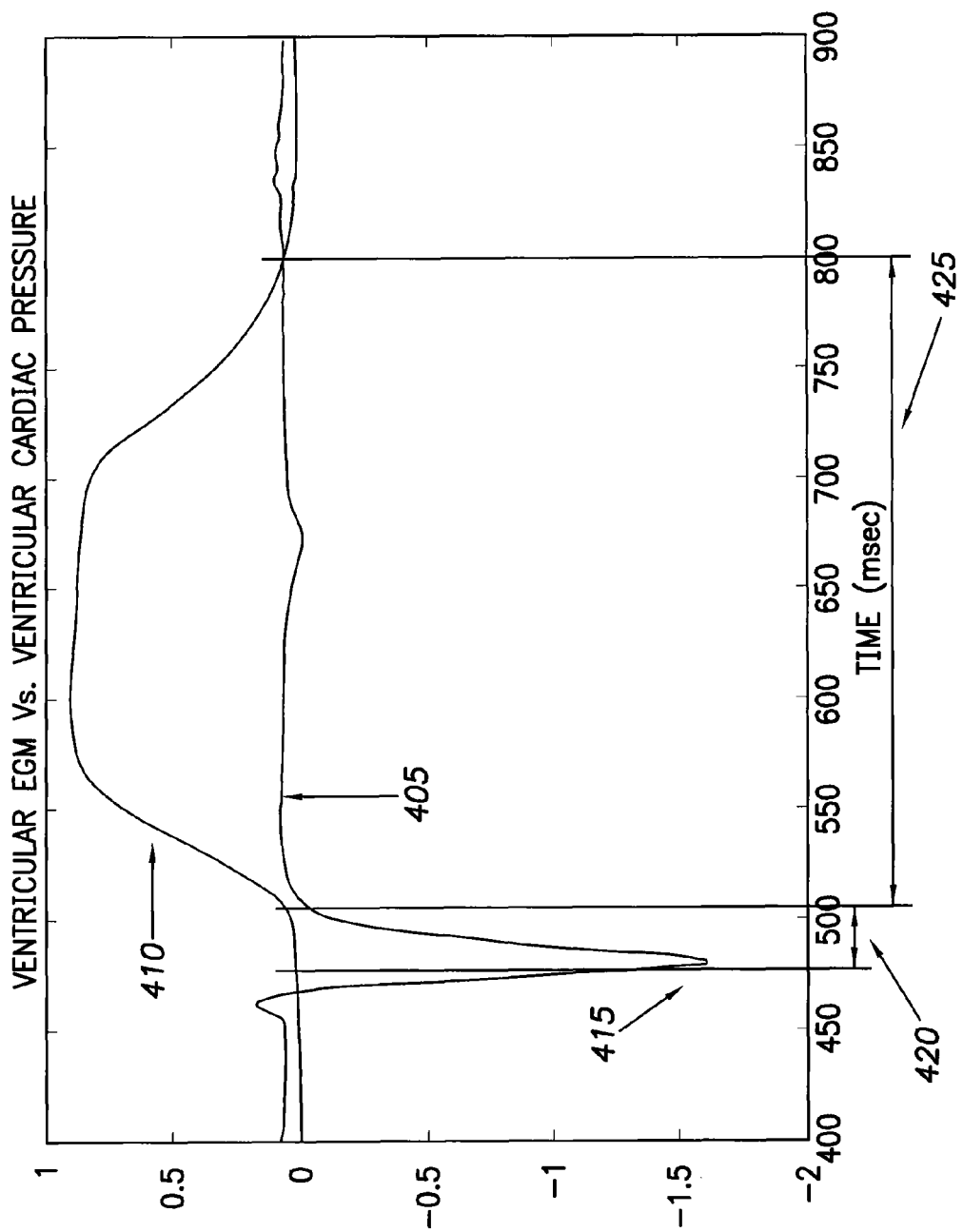
FIG. 4 illustrates traces of example ventricular EGM and ventricular cardiac pressure signals versus time.

For example, FIG. 4 illustrates a trace of an example first signal 405 indicative of ventricular cardiac electrical activity and an example second signal 410 indicative of ventricular cardiac pressure. As shown in FIG. 4, the timing of second signal 410 can be obtained in relation to first signal 405. A delay 420 of approximately 20 to 30 milliseconds exists between electrical activation, illustrated by R-wave 415 of first signal 405, and the initiation of mechanical contraction of the heart (mechanical contraction of the heart corresponds to time period 425), illustrated by rising and falling portions of second signal 410. During interval 420 (i.e., the R-wave) of first signal 405, second signal 410 maintains an approximately constant value. In particular, the value of second signal 410 during the peak of the R-wave of first signal 405 can be used as the baseline value with which subsequent values of second signal 410 can be normalized.

After normalizing the second signal, the normalized second signal is then referenced at step 318 to a reference signal (e.g., value) to produce a referenced second signal (referred to herein simply as a "referenced signal"). For example, a reference signal can be subtracted from the normalized second signal to produce the referenced signal. The reference signal, for example, can be a historical measurement of the normalized second signal to which subsequent measurements of the normalized second signal are compared for the purpose of detecting a change indicative of ischemia. Appropriate reference values and intervals at which ischemia diagnoses are attempted vary depending on the application. For example, in an embodiment, the second signal is measured periodically, such as every hour, for the purposes of generating a long-term diagnostic record. In this case, a reference value determined at a single point in time (e.g., at the time of implant or at the command of a clinician) or an average of reference values determined over a relatively long period of time (e.g., over the previous week) is appropriate. In another embodiment, the second signal is measured more frequently, such as every thirty seconds, for the purposes of acute ischemia event detection. In this case, a more appropriate reference value is determined from a relatively recent history (e.g., a moving average of values measured over the previous hour).

After referencing the second signal, an average value or a peak value of the referenced second signal over a predetermined interval of the first signal is monitored in step 320 for a change. If the average or peak value of the referenced second signal over the predetermined interval of the first signal decreases, then an ischemia is indicated in step 325, otherwise, monitoring continues and steps 305-320 are repeated.

In an embodiment, after referencing the second signal based on an appropriate reference value, an ischemia event is indicated based on a comparison of a referenced signal measurement (e.g., peak value, average value, etc.) to a threshold value. In one example, only one referenced signal measurement is compared to the threshold to indicate an ischemia event. In another example, several consecutive referenced signal measurements (e.g., three) must exceed the threshold before indicating an ischemia event. In yet another example, a rate at which the referenced signal measurements exceed a first threshold must exceed a second threshold (e.g., at least three of five consecutive measurements) before indicating an ischemia event. In a further example, a measure of statistical significance (e.g., T-statistic) between the reference value and subsequent referenced signal measurements must also exceed a threshold before indicating an ischemia event.

In an embodiment, step 320 of FIG. 3 is implemented with ischemia detector 220 of FIG. 2. As described above, ischemia detector 220 is configured to receive a signal indicative of cardiac electrical activity, such as signals 221, 223 and 224, and a signal indicative of ventricular cardiac pressure, such as signal 222. For each cardiac cycle, ischemia detector 220 normalizes signal 222 based on a baseline value, references the normalized signal to a historical reference value and monitors the referenced signal for a decrease over a predetermined interval of the signal indicative of cardiac electrical activity. In an embodiment, ischemia detector 220 compares an average value of the referenced signal to a threshold value to determine whether to indicate an ischemia or to continue monitoring. In another embodiment, ischemia detector 220 compares a peak value of the referenced signal to a threshold value to determine whether to indicate an ischemia or to continue monitoring.

As will be apparent to one skilled in the art, there are several methods essentially equivalent to the method described above which yield essentially the same results, yet which may have advantages over the method described above. For example, in an embodiment, the second signal is averaged over the predetermined interval of the first signal within the same step in which the second signal is normalized. In this embodiment a reference signal may be stored as a single average value rather than as set of samples, thus reducing the amount memory required in an ICRMD.

For example, FIGS. 5A-5E illustrates traces showing the results of a simulation during which an ischemia was induced in a canine using a balloon catheter. The traces shown in FIGS. 5A-5E illustrate changes in average cardiac pressure versus cardiac cycle number (i.e., the number of elapsed beats) for five different time intervals relative to a cardiac electrical activity signal. Interval 1 corresponds to a time interval from approximately 50-100 milliseconds (msec) after a peak of an R-wave of the cardiac electrical activity signal, Interval 2 from approximately 100-150 msec, Interval 3 from approximately 150-200 msec, Interval 4 from approximately 200-250 msec, and Interval 5 from approximately 250-300 msec. Intervals 1-3 roughly correspond to the ST segment of the cardiac electrical activity signal, with Interval 3 corresponding largely to the T-wave of the cardiac electrical activity signal.

Segments a-g of the average cardiac pressure signal are also shown in FIGS. 5A-5E. Segment a corresponds to average cardiac pressure before ischemia is induced by inflating the balloon catheter, segment b corresponds to average cardiac pressure during approximately 0-1 minute of ischemia, segment c during approximately 1-2 minutes of ischemia, segment d during approximately 2-3 minutes of ischemia, segment e during approximately 3-4 minutes of ischemia, segment f during approximately 4-5 minutes of ischemia, and segment g corresponds to average cardiac pressure approximately 1 minute after deflating the balloon catheter.

Figure 5A:
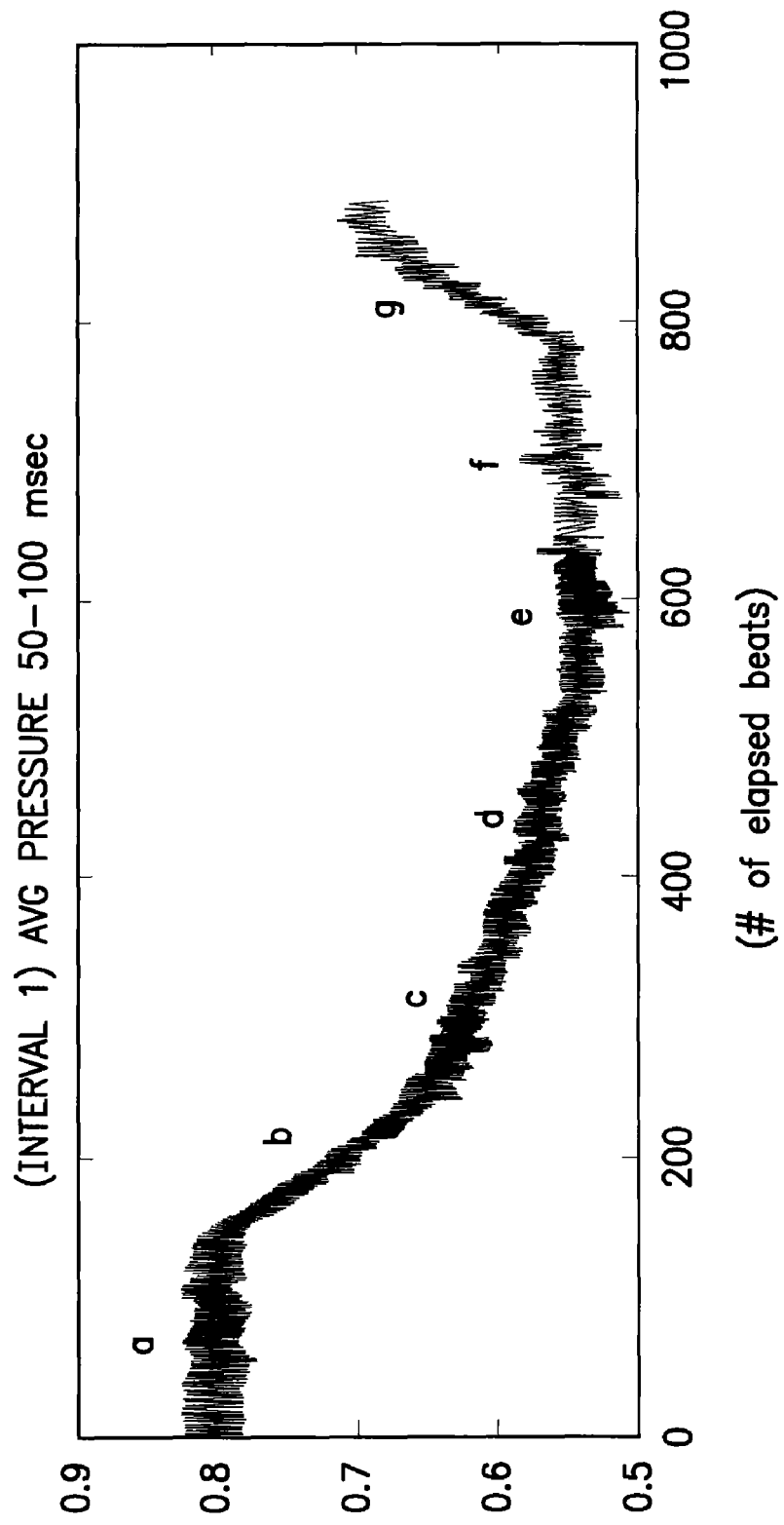
FIG. 5A-5E illustrates traces, for five different time intervals, of example average cardiac pressure signals versus cardiac cycle number.
Figure 5B:
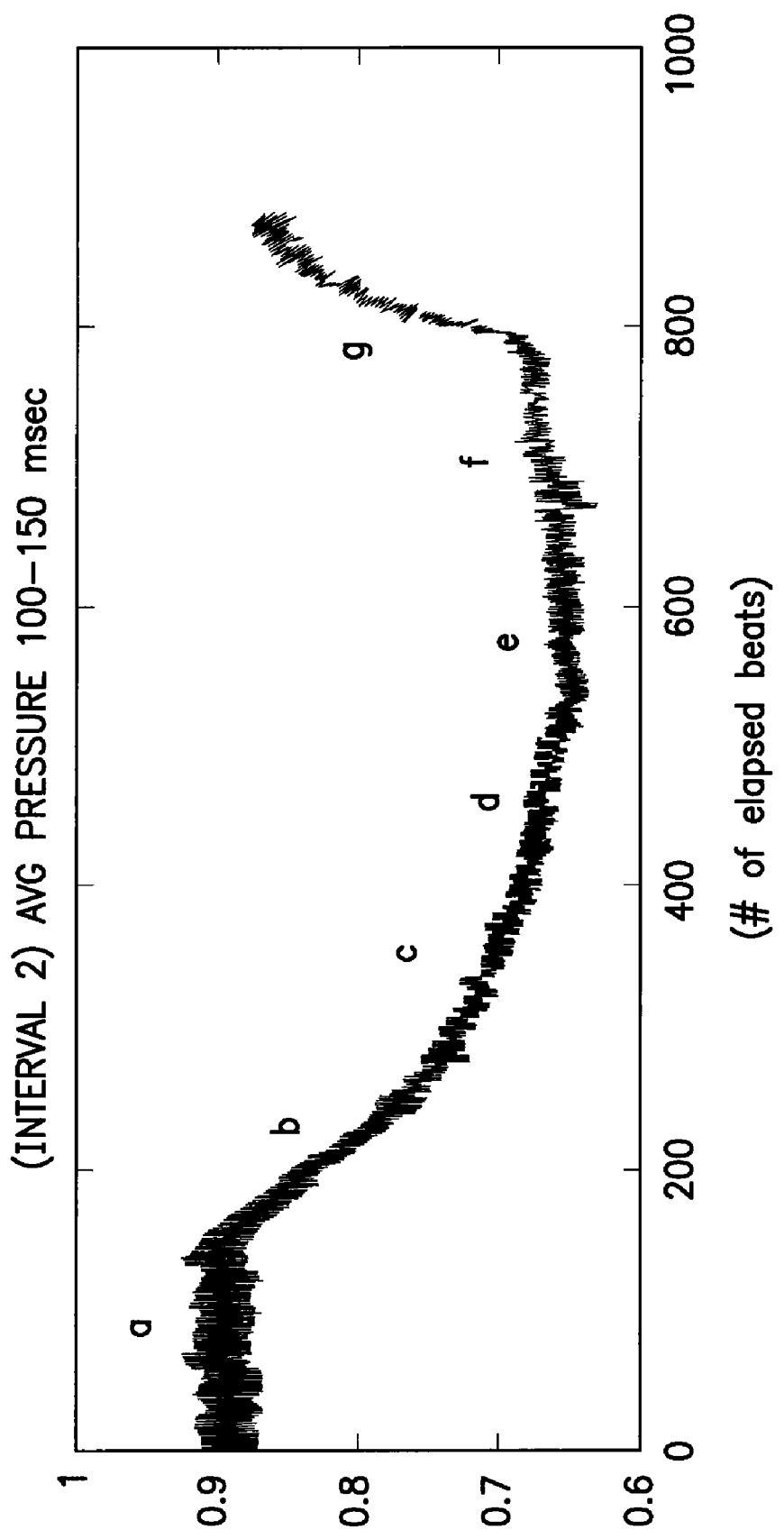
Figure 5C:
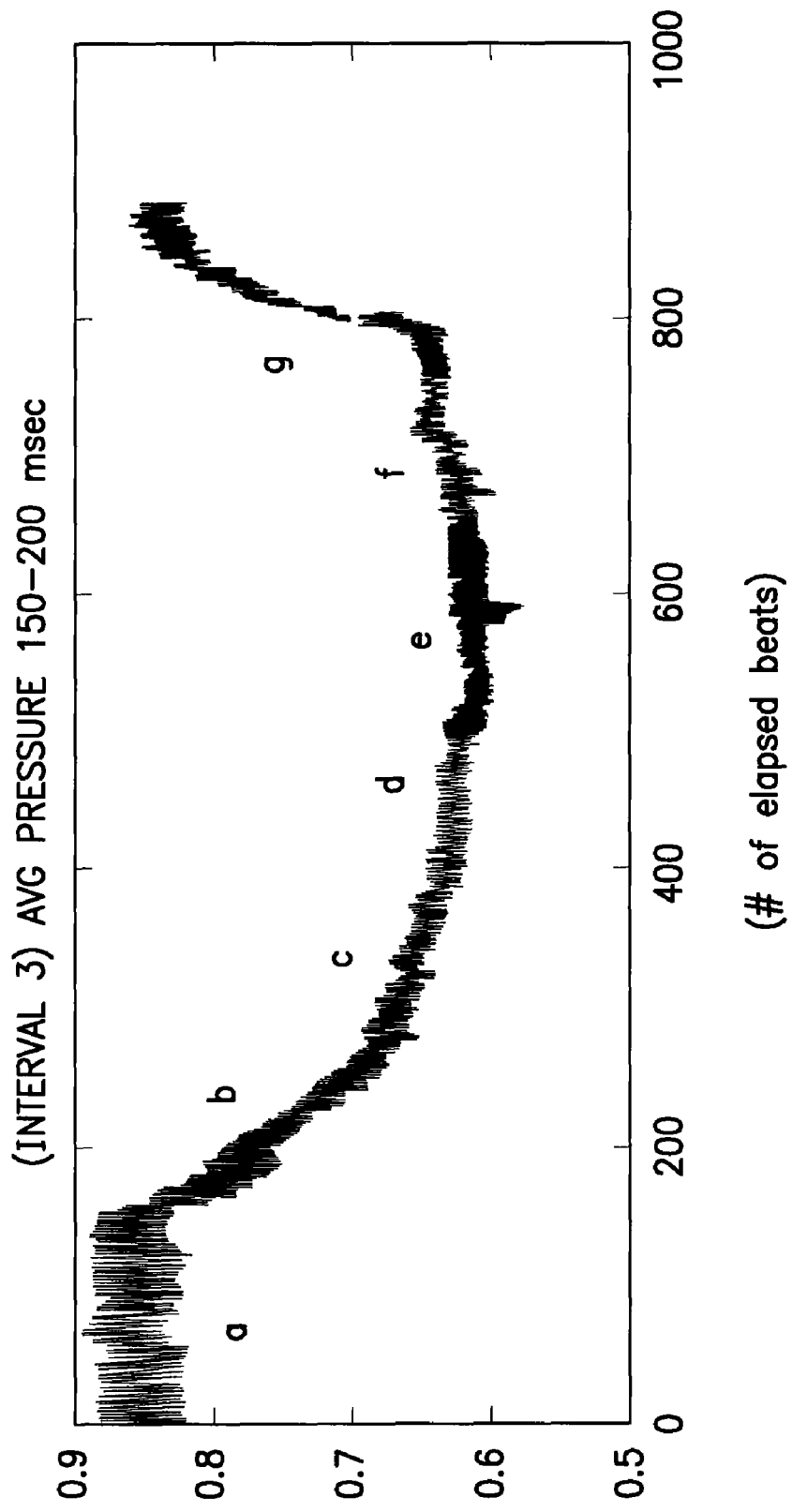
Figure 5D:
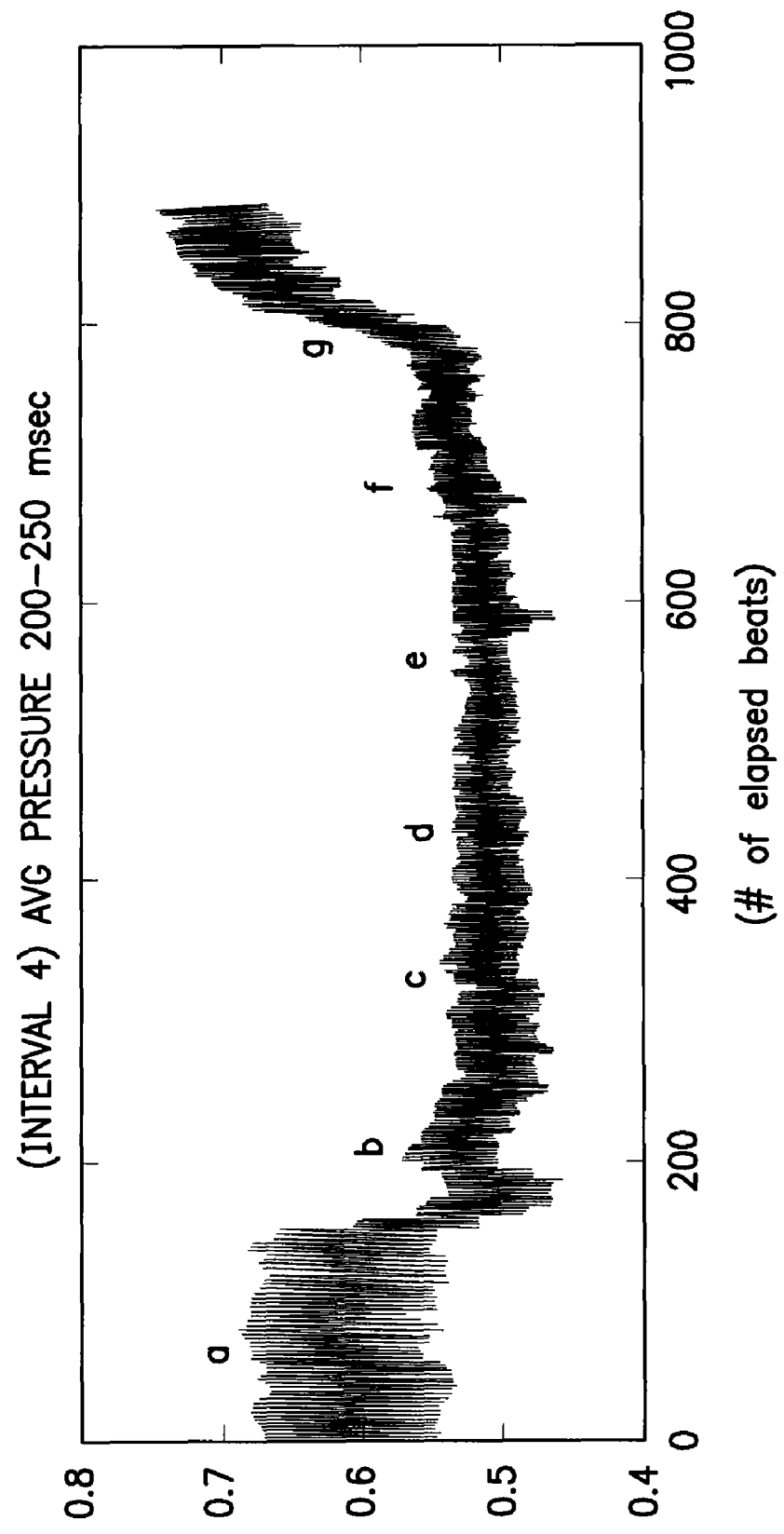
Figure 5E:
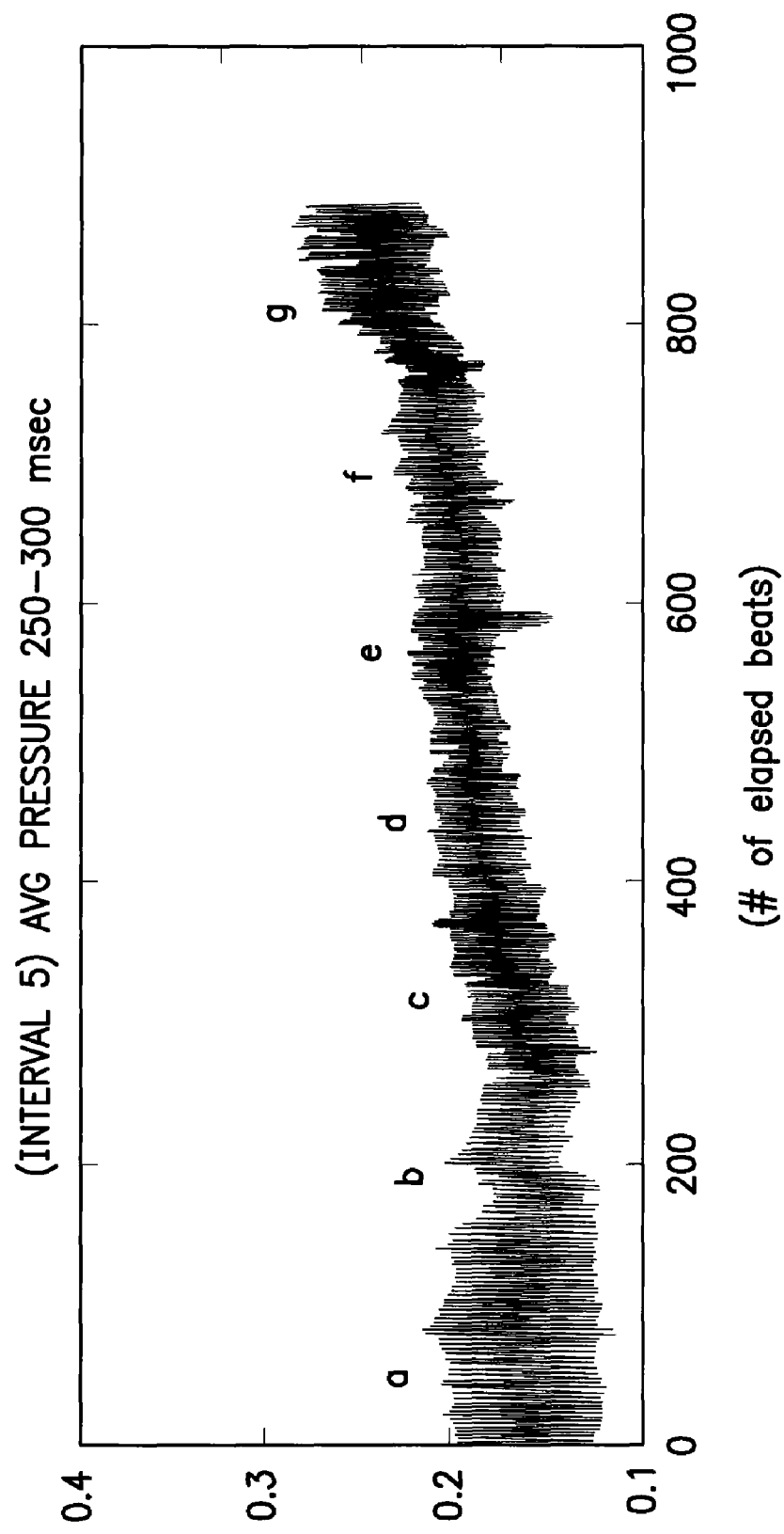

FIGS. 5A-5C illustrates significant attenuation of the average cardiac pressure signal during ischemia (segments b-f) as compared to FIGS. 5D and 5E. Thus, FIGS. 5A-5C demonstrate that, during ischemia, average cardiac pressure changes most significantly (i.e., is attenuated) during Intervals 1-3. As described above, Intervals 1-3 correspond to the time period from approximately 50-200 msec after the peak of the R-wave of the cardiac electrical activity signal, which roughly corresponds to the ST segment of the cardiac electrical activity signal. In comparison, FIGS. 5D and 5E demonstrate that, during ischemia, average cardiac pressure does not change significantly (i.e., is not attenuated) during Intervals 4 and 5. As described above, Intervals 4 and 5 correspond to the time period from approximately 200-300 msec after the peak of the R-wave of the cardiac electrical activity signal.

While FIGS. 5A-5E illustrate changes in average cardiac pressure during an ischemia, in another embodiment, changes in peak cardiac pressure (i.e., instead of average cardiac pressure) can be monitored during the relevant time intervals of a corresponding cardiac electrical activity signal to detect an ischemia, according to step 320 of FIG. 3. Therefore, monitoring average cardiac pressure or peak cardiac pressure for attenuation during the earlier time intervals following an R-wave (e.g., during the ST segment) of a corresponding cardiac electrical activity signal is a valuable diagnostic tool for indicating an ischemia.

FIG. 6 shows a process flowchart 600 providing steps for detecting ischemia using an ICRMD to monitor characteristics of a signal indicative of cardiac pressure. In step 605, a first signal indicative of cardiac electrical activity is acquired. For example, as described above with respect to FIG. 2, data acquisition system 290 is configured to acquire cardiac electrical activity data and provide an output signal 221 indicative of cardiac electrical activity to ischemia detector 220. Alternatively, or in addition to data acquisition system 290, atrial and ventricular sensing circuits 282 and 284 can include dedicated sense amplifiers to directly sense cardiac electrical activity signal events (e.g., an R-wave, etc.) and provide output signals 223 and 224 indicative of cardiac electrical activity to ischemia detector 220.

In step 610, a second signal indicative of cardiac pressure is acquired. For example, as described above with respect to FIG. 2, physiologic sensor 208 can be configured to acquire ventricular cardiac pressure data via a pressure transducer or other type of sensor and provide an output signal 222 indicative of ventricular cardiac pressure to ischemia detector 220.

In step 615, during each cardiac cycle, a derivative signal is generated that is a first derivative of the second signal, and a peak value of the derivative signal is determined.

In step 620, the peak value of the derivative signal is monitored for attenuation over a predetermined interval of the first signal. If the peak value of the derivative signal is attenuated over the predetermined interval of the first signal, then an ischemia is indicated in step 625. Otherwise, monitoring continues and steps 605-620 of process 600 are repeated.

The peak value of the derivative signal can be measured on an ensemble-average of several (e.g., 8-16) consecutive or approximately consecutive derivative signal measurements. Alternatively, the peak value of the derivative signal can be measured for each of several individual consecutive or approximately consecutive derivative signal measurements, and a statistical measurement, such as the mean and the variance, can be calculated on the several measurements.

In an embodiment, an ischemia event is indicated based on comparing a measurement of the peak value of the derivative signal to a threshold value. In one example, only one peak value measurement is compared to the threshold to indicate an ischemia event. In another example, several consecutive peak value measurements (e.g., three) must exceed the threshold before indicating an ischemia event. In yet another example, a rate at which the peak value measurements exceed a first threshold must exceed a second threshold (e.g., at least three of five consecutive measurements) before indicating an ischemia event. In a further example, a measure of statistical significance (e.g., T-statistic) relating to the peak value measurement must exceed a threshold before indicating an ischemia event.

In an embodiment, steps 615-625 are implemented using ischemia detector 220 of FIG. 2. As described above, ischemia detector 220 is configured to receive a signal indicative of cardiac electrical activity, such as signals 221, 223 and 224, and a signal indicative of ventricular cardiac pressure, such as signal 222. During each cardiac cycle, ischemia detector 220 generates a derivative signal, which is a first derivative of cardiac pressure signal 222, and determines a peak value of the derivative signal. In this example, ischemia detector 220 monitors the peak value of the derivative signal for attenuation over a predetermined interval of the signal indicative of electrical activity based on a comparison to a threshold value.

During an ischemia, the contractility of cardiac myocytes in the ischemic zone is expected to be compromised. Accordingly, the peak value of a derivative signal (i.e., $dP/dt_{max}$), which is a first derivative of a signal indicative of cardiac pressure, is likewise expected to be reduced or attenuated during an ischemia.

Figure 7:
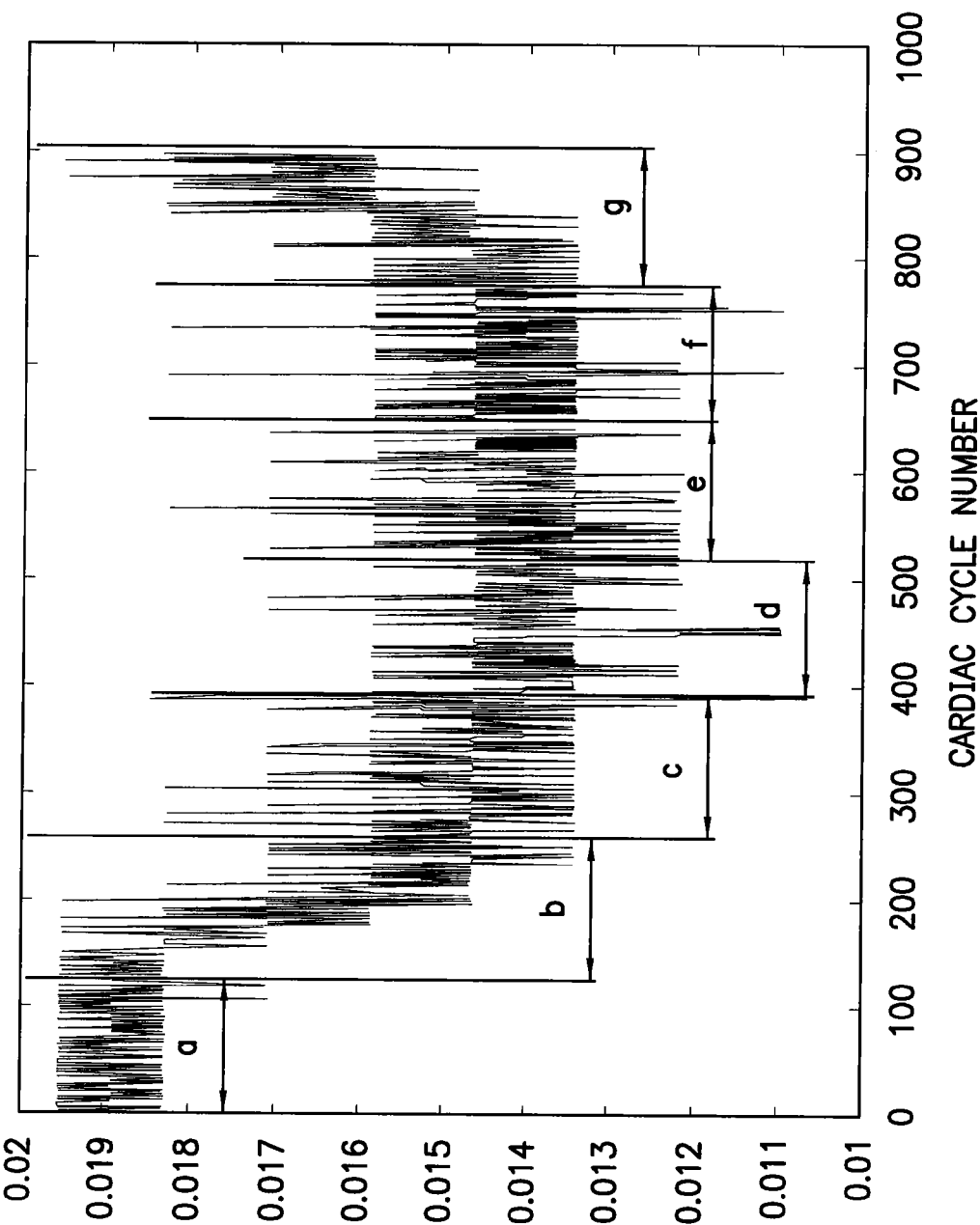
FIG. 7 illustrates a trace of an example peak derivative cardiac pressure signal versus cardiac cycle number.

For example, FIG. 7 illustrates a trace of an example $dP/dt_{max}$ signal versus cardiac cycle number (i.e., the number of elapsed beats) for a simulation during which an ischemia was induced in a canine using a balloon catheter. Segment a of the $dP/dt_{max}$ signal corresponds to $dP/dt_{max}$ before ischemia is induced by inflating the balloon catheter, segment b corresponds to $dP/dt_{max}$ during approximately 0-1 minute of ischemia, segment c during approximately 1-2 minutes of ischemia, segment d during approximately 2-3 minutes of ischemia, segment e during approximately 3-4 minutes of ischemia, segment f during approximately 4-5 minutes of ischemia, and segment g corresponds to $dP/dt_{max}$ approximately 1 minute after the balloon catheter is deflated.

Segment b of the $dP/dt_{max}$ signal shown in FIG. 7 illustrates significant attenuation of the $dP/dt_{max}$ signal when ischemia is induced. Segments c-f illustrates continued attenuation of the $dP/dt_{max}$ signal for the duration of the ischemia. Segment g illustrates a return of the $dP/dt_{max}$ signal to its pre-ischemic amplitude (shown in segment a) when the blood supply is restored upon deflation of the balloon catheter.

Method 600 is advantageous because detecting ischemia based on a derivative signal, which is a first derivative of a signal indicative of cardiac pressure, greatly reduces the effect of any DC offset in the system. Accordingly, unlike method 300 described above, method 600 does not require normalizing the signal indicative of cardiac pressure prior to analyzing the signal for attenuation. The derivative signal may be compared directly to a predetermined threshold, or it may be referenced to a historical reference signal as described above, with the resulting referenced signal being compared to a threshold.

Analysis of Delay in Cardiac Pressure Signal with Respect to Electrical Signal In this section, example techniques are described for analyzing delay of a cardiac pressure signal with respect to cardiac electrical activity signal events to detect ischemia. In a first example, ischemia detector 220 indicates an ischemia based on a comparison of a delay from a predetermined portion of a cardiac electrical activity signal to a peak value of a cardiac pressure signal with a predetermined value. In a second example, ischemia detector 220 indicates an ischemia based on a comparison of delay from a predetermined portion of a cardiac electrical activity signal to a peak value of a derivative cardiac pressure signal with a predetermined value.

Figure 8:
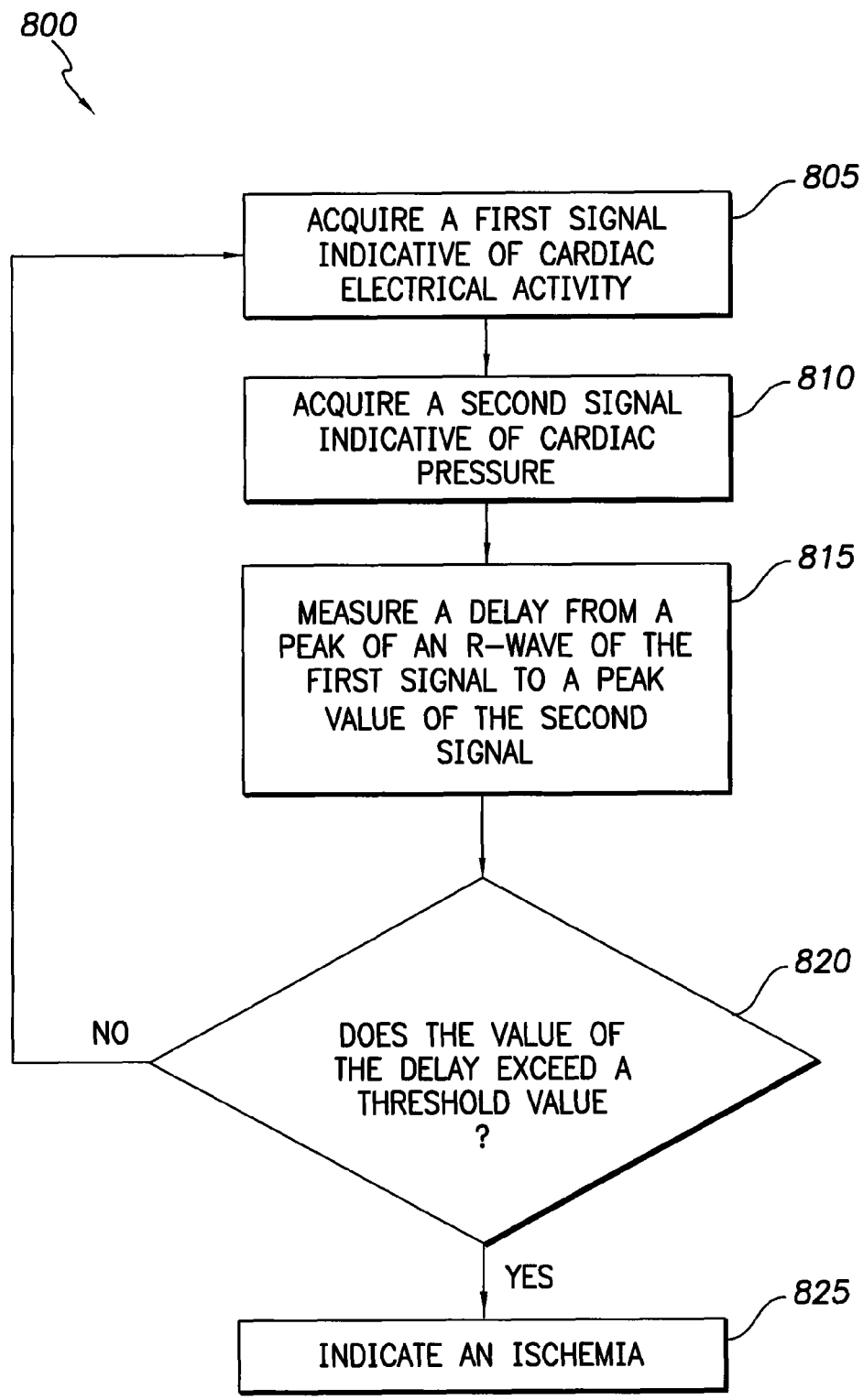
FIG. 8 is a process flowchart providing example steps for detecting ischemia using an ICRMD to monitor characteristics of a cardiac pressure signal.
Figure 10:
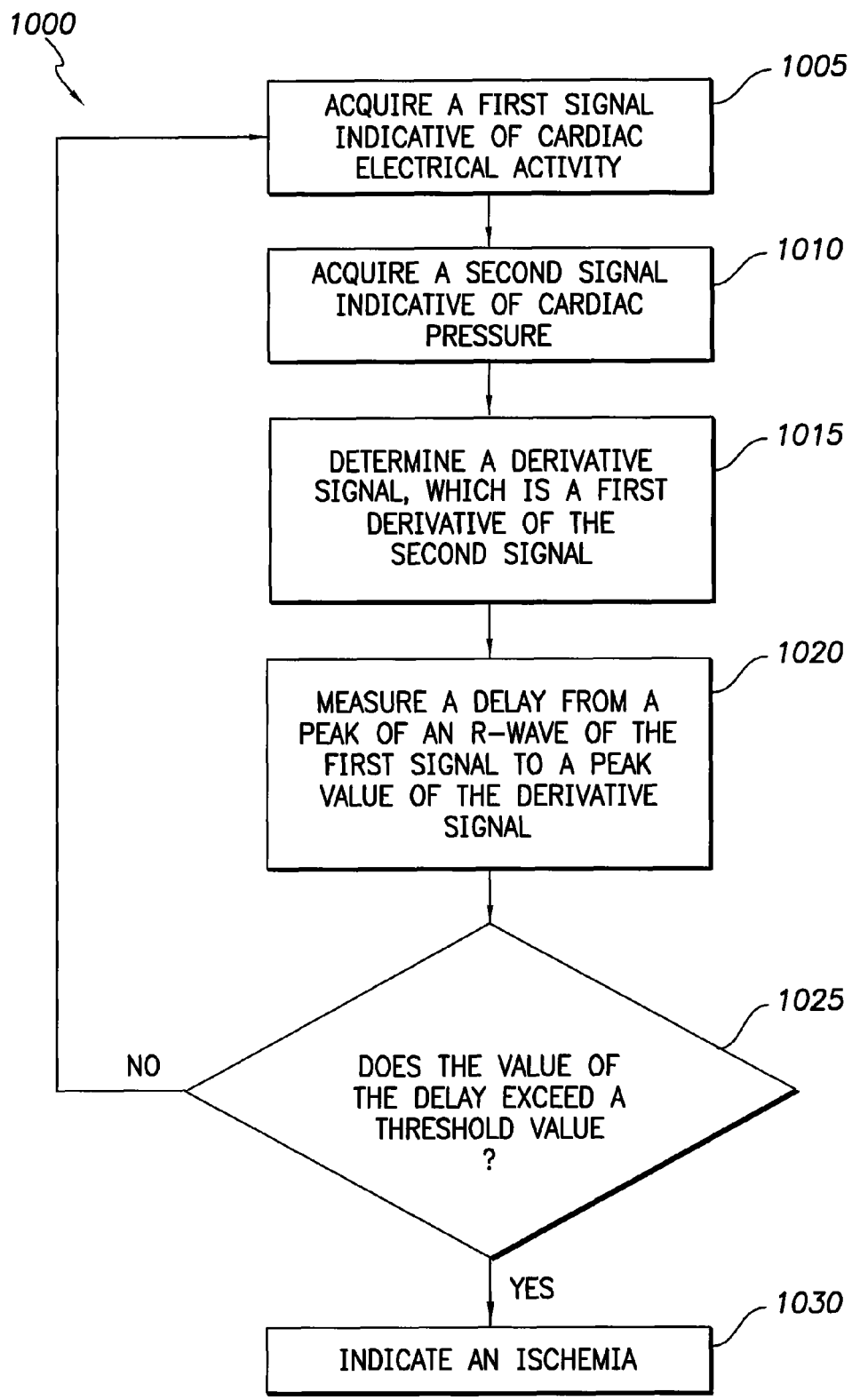
FIG. 10 is a process flowchart providing example steps for detecting ischemia using an ICRMD to monitor characteristics of a derivative cardiac pressure signal.

FIGS. 8 and 10 show process flowcharts providing example steps for detecting myocardial ischemia using an ICRMD. The steps of FIGS. 8 and 10 do not necessarily have to occur in the order shown, as will be apparent to persons skilled in the relevant art(s) based on the teachings herein. Other operational and structural embodiments will be apparent to persons skilled in the relevant art(s) based on the following discussion. These steps are described in detail below.

FIG. 8 shows a process flowchart 800 providing steps for detecting ischemia using an ICRMD to monitor characteristics of a signal indicative of cardiac pressure. In step 805, a first signal indicative of cardiac electrical activity is acquired. For example, as described above with respect to FIG. 2, data acquisition system 290 is configured to acquire cardiac electrical activity data and provide an output signal 221 indicative of cardiac electrical activity to ischemia detector 220. Alternatively, or in addition to data acquisition system 290, atrial and ventricular sensing circuits 282 and 284 can include dedicated sense amplifiers to directly sense cardiac electrical activity signal events (e.g., an R-wave, etc.) and provide output signals 223 and 224 indicative of cardiac electrical activity to ischemia detector 220.

In step 810, a second signal indicative of cardiac pressure is acquired. For example, as described above with respect to FIG. 2, physiologic sensor 208 can be configured to acquire ventricular cardiac pressure data via a pressure transducer or other type of sensor and provide an output signal 222 indicative of ventricular cardiac pressure to ischemia detector 220.

In step 815, during each cardiac cycle, a time delay (e.g., in milliseconds) is measured from a peak of an R-wave of the first signal to a peak value of the second signal. The time delay can be measured on an ensemble-average of cardiac pressure signal measurements. Alternatively, the time delay can be measured on each of several individual consecutive or approximately consecutive cardiac pressure signal measurements, and a statistical measurement, such as the mean and the variance, can be calculated on the several measurements.

Because during an ischemia, the contractility of cardiac myocytes in the ischemic zone is expected to be compromised, the time delay between peak electrical activation and peak mechanical activation is expected to increase. Thus, in step 820, the value of the delay is compared to a threshold value (e.g., the value of the delay between peak electrical and mechanical activation during a non-ischemic period). If the value of the delay exceeds the threshold value, then an ischemia is indicated in step 825. Otherwise, monitoring continues and steps 805-820 of process 800 are repeated.

In one example, only one delay measurement is compared to the threshold to indicate an ischemia event. In another example, several consecutive delay measurements (e.g., three) must exceed the threshold before indicating an ischemia event. In yet another example, a rate at which the delay measurements exceed a first threshold must exceed a second threshold (e.g., at least three of five consecutive measurements) before indicating an ischemia event. In a further example, a measure of statistical significance (e.g., T-statistic) relating to the delay measurement must exceed a threshold before indicating an ischemia event.

In an embodiment, steps 815-825 are implemented using ischemia detector 220 of FIG. 2. As described above, ischemia detector 220 is configured to receive a signal indicative of cardiac electrical activity, such as signals 221, 223 and 224, and a signal indicative of ventricular cardiac pressure, such as signal 222. During each cardiac cycle, ischemia detector 220 measures a time delay between peak electrical and mechanical activation, such as the time delay between a peak of an R-wave of the cardiac electrical activity signal and a peak value of the cardiac pressure signal. In this example, ischemia detector 220 compares the value of the delay to a threshold value, such as the value of the delay between peak electrical and mechanical activation during a non-ischemic period, to determine whether to indicate an ischemia.

The delay can also be measured from the sensed R-wave event or the maximum value of dV/dt of the electrical event (i.e., the first derivative of the electrical signal), to the peak of the pressure signal or the peak of dP/dt (i.e., the first derivative of the pressure signal).

Figure 9:
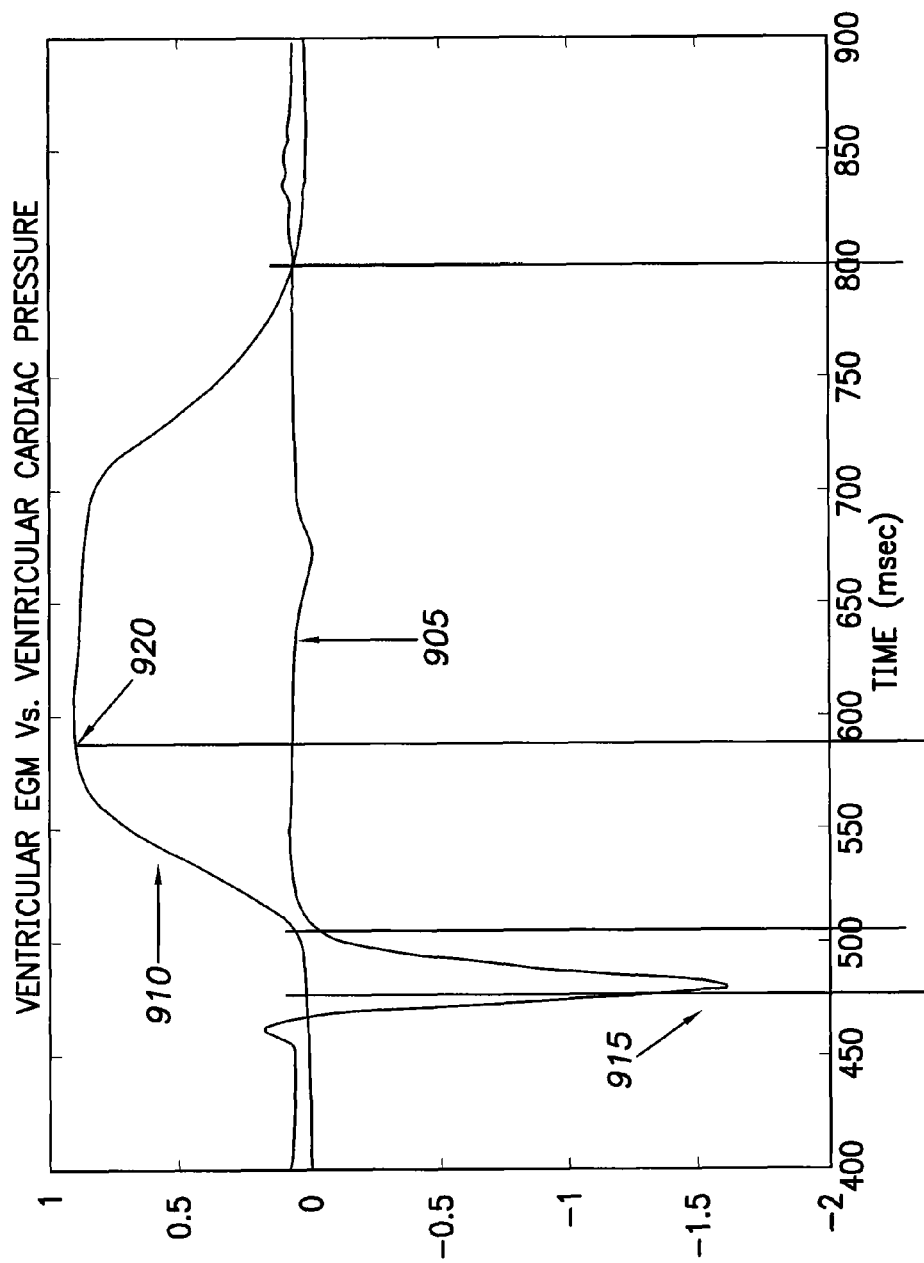
FIG. 9 illustrates traces of example ventricular EGM and ventricular cardiac pressure signals versus time.

For example, FIG. 9 illustrates example traces of a cardiac pressure signal 910 and a cardiac electrical activity signal 905 versus time (in milliseconds). Also shown in FIG. 9, is a time delay 900 between a peak of an R-wave 915 of electrical activity signal 905 and a peak value 920 of pressure signal 910. During an ischemia, the value of delay 900 is expected to increase as compared to the value of delay 900 during a non-ischemic period.

FIG. 10 shows a process flowchart 1000 providing steps for detecting ischemia using an ICRMD to monitor characteristics of a derivative cardiac pressure signal. In step 1005, a first signal indicative of cardiac electrical activity is acquired. For example, as described above with respect to FIG. 2, data acquisition system 290 is configured to acquire cardiac electrical activity data and provide an output signal 221 indicative of cardiac electrical activity to ischemia detector 220. Alternatively, or in addition to data acquisition system 290, atrial and ventricular sensing circuits 282 and 284 can include dedicated sense amplifiers to directly sense cardiac electrical activity signal events (e.g., an R-wave, etc.) and provide output signals 223 and 224 indicative of cardiac electrical activity to ischemia detector 220.

In step 1010, a second signal indicative of cardiac pressure is acquired. For example, as described above with respect to FIG. 2, physiologic sensor 208 can be configured to acquire ventricular cardiac pressure data via a pressure transducer or other type of sensor and provide an output signal 222 indicative of ventricular cardiac pressure to ischemia detector 220.

In step 1015, during each cardiac cycle, a derivative signal is generated that is a first derivative of the second signal.

In step 1020, during each cardiac cycle, a time delay (e.g., in milliseconds) is measured from a peak of an R-wave of the first signal to a peak value of the derivative signal. The time delay can be measured on an ensemble-average of several (e.g., 8-16) consecutive or approximately consecutive derivative signal measurements. Alternatively, the time delay can be calculated on each of several individual consecutive or approximately consecutive derivative signal measurements, and a statistical measurement, such as the mean and the variance, can be calculated on the several measurements.

Because during an ischemia, the contractility of cardiac myocytes in the ischemic zone is expected to be compromised, the time delay between peak electrical activation and peak mechanical activation is expected to increase. Thus, in step 1025, the value of the delay is compared to a threshold value (e.g., the value of the delay between peak electrical activation and peak mechanical activation during a non-ischemic period). If the value of the delay exceeds the threshold value, then an ischemia is indicated in step 1030. Otherwise, monitoring continues and steps 1005-1025 of process 1000 are repeated.

In one example, only one delay measurement is compared to the threshold to indicate an ischemia event. In another example, several consecutive delay measurements (e.g., three) must exceed the threshold before indicating an ischemia event. In yet another example, a rate at which the delay measurements exceed a first threshold must exceed a second threshold (e.g., at least three of five consecutive measurements) before indicating an ischemia event. In a further example, a measure of statistical significance (e.g., T-statistic) relating to the delay measurement must exceed a threshold before indicating an ischemia event.

In an embodiment, steps 1015-1030 are implemented using ischemia detector 220 of FIG. 2. As described above, ischemia detector 220 is configured to receive a signal indicative of cardiac electrical activity, such as signals 221, 223 and 224, and a signal indicative of ventricular cardiac pressure, such as signal 222. During each cardiac cycle, ischemia detector 220 generates a derivative signal, which is a first derivative with respect to time of cardiac pressure signal 222, and measures a time delay between peak electrical activation and peak mechanical activation, such as the time delay between a peak of an R-wave of the cardiac electrical activity signal and a peak value of the derivative signal. In this example, ischemia detector 220 compares the value of the delay to a threshold value, such as the value of the delay between peak electrical activation and peak mechanical activation during a non-ischemic period, to determine whether to indicate an ischemia. The value of the delay may also be compared to a historical reference value and the resulting referenced value compared to a threshold.

Morphology of Cardiac Pressure Signal

In this section, example techniques are described for analyzing cardiac pressure signal morphology to detect ischemia. In a first example, ischemia is diagnosed based on analysis of a ratio of a height (i.e., amplitude) of the cardiac pressure signal to a width (i.e., duration) of the cardiac pressure signal. In a second example, ischemia is diagnosed based on morphology of a derivative cardiac pressure signal, which is a first derivative of the cardiac pressure signal. In this case, ischemia is indicated based on analysis of a ratio of a maximum value of a positive (i.e., rising) portion of the derivative cardiac pressure signal to a maximum value of a negative (i.e., falling) portion of the derivative cardiac pressure signal.

Figure 11:
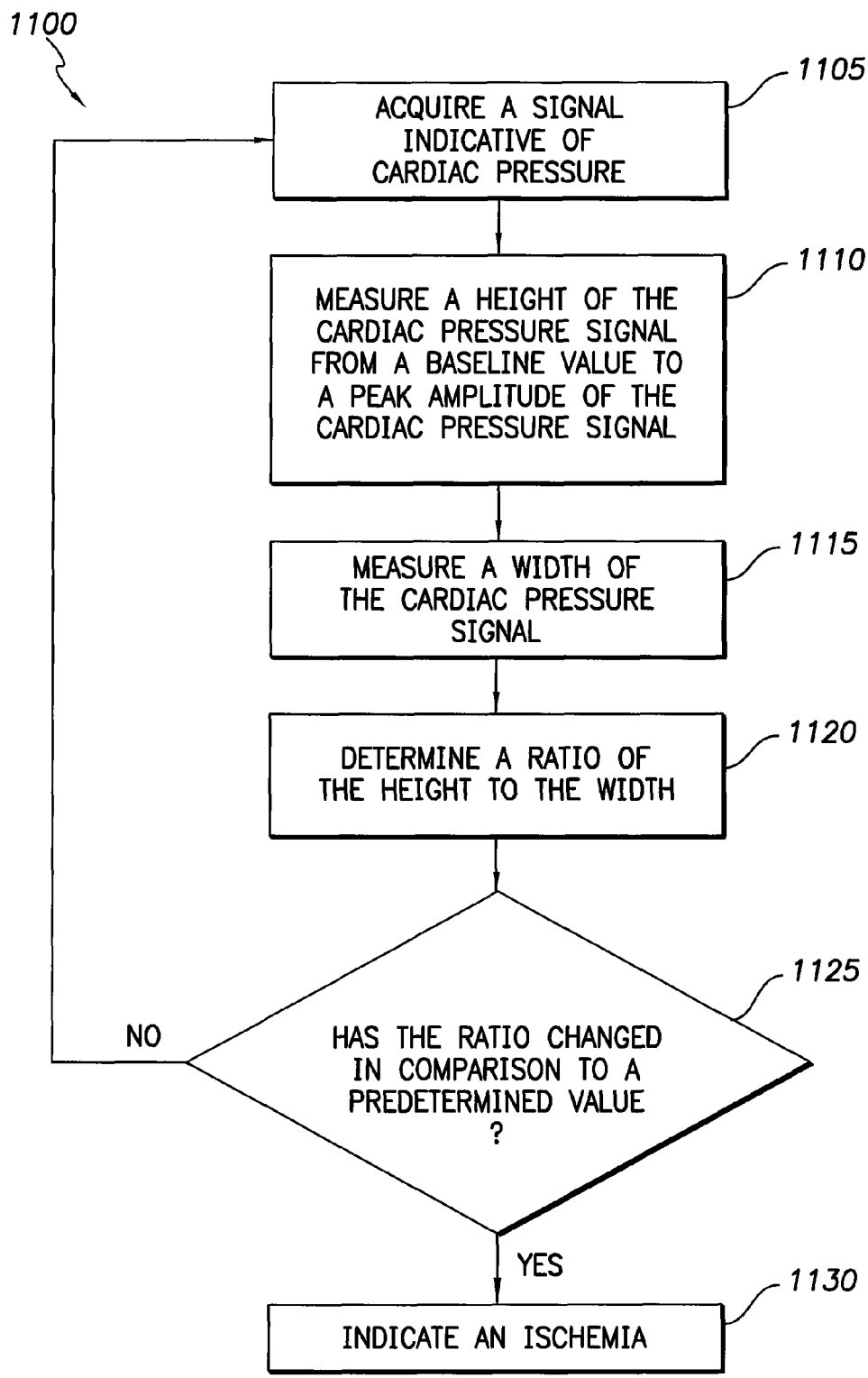
FIG. 11 is a process flowchart providing example steps for detecting ischemia using an ICRMD to monitor characteristics of a cardiac pressure signal.

FIGS. 11 and 13 show process flowcharts providing example steps for detecting myocardial ischemia using an ICRMD. The steps of FIGS. 11 and 13 do not necessarily have to occur in the order shown, as will be apparent to persons skilled in the relevant art(s) based on the teachings herein. Other operational and structural embodiments will be apparent to persons skilled in the relevant art(s) based on the following discussion. These steps are described in detail below.

FIG. 11 shows a process flowchart 1100 providing steps for detecting ischemia using an ICRMD to analyze morphology of a signal indicative of cardiac pressure. In step 1105, a signal indicative of cardiac pressure is acquired. For example, as described above with respect to FIG. 2, physiologic sensor 208 can be configured to acquire ventricular cardiac pressure data via a pressure transducer or other type of sensor and provide an output signal 222 indicative of ventricular cardiac pressure to ischemia detector 220.

Figure 12:
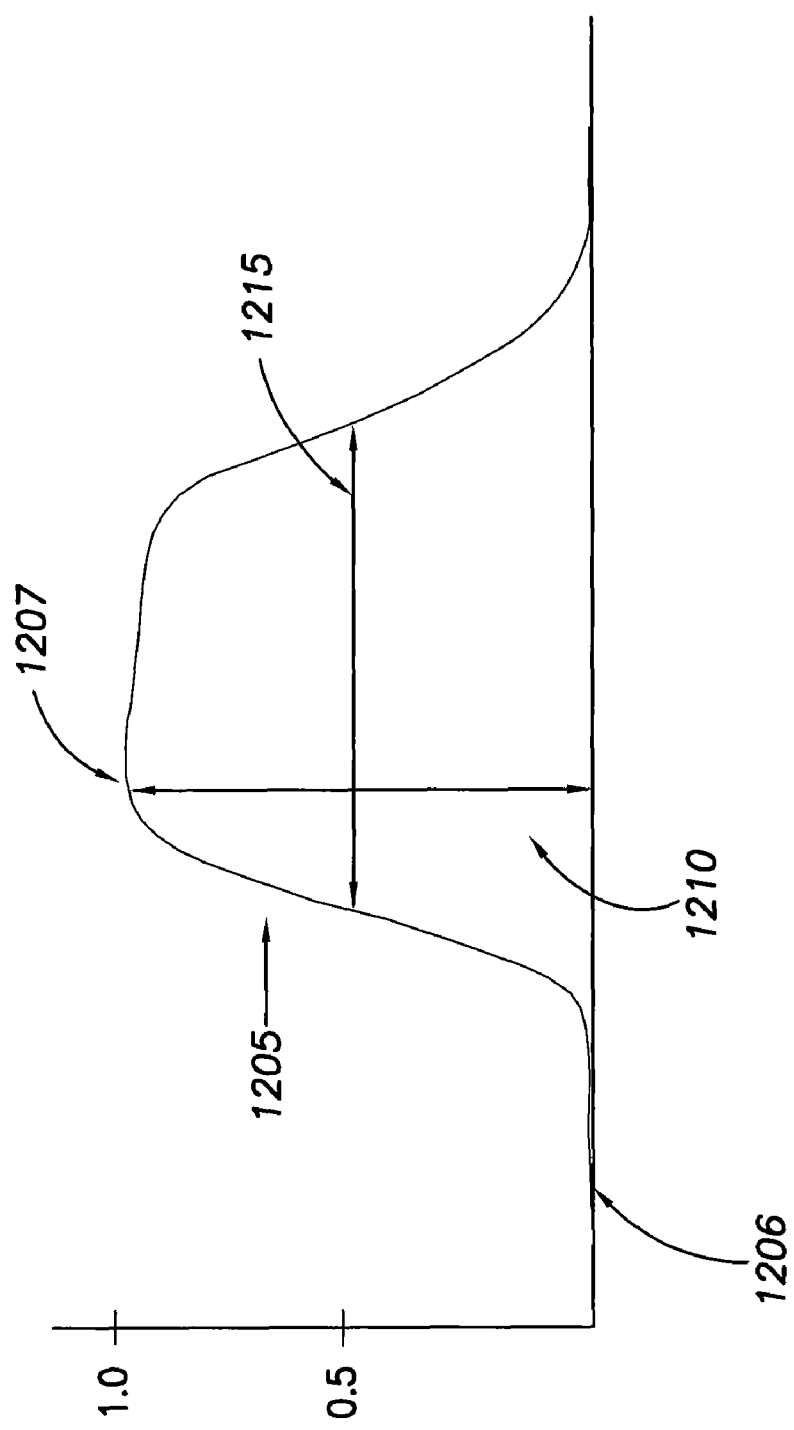
FIG. 12 illustrates a trace of an example cardiac pressure signal.

In step 1110, a height of the cardiac pressure signal is measured from a baseline value to a peak amplitude of the cardiac pressure signal. For example, FIG. 12 illustrates an example trace of a cardiac pressure signal 1205. As shown in FIG. 12, a height 1210 is measured from a baseline value 1206 of cardiac pressure signal 1205 to a peak amplitude 1207 of cardiac pressure signal 1205.

In step 1115, a width (i.e., duration) of the cardiac pressure signal is measured. For example, as shown in FIG. 12, a width 1215 is measured of cardiac pressure signal 1205. In one embodiment, the width is measured at a particular amplitude of the cardiac pressure signal. For example, the width can be measured at an amplitude that is about fifty percent (or any other percentage) of the peak amplitude of the cardiac pressure signal. In FIG. 12, width 1215 is measured at an amplitude that is fifty percent of peak amplitude 1207 of cardiac pressure signal 1205.

In step 1120, a ratio of the height to the width of the cardiac pressure signal is determined. The height/width ratio can be measured on an ensemble-average of several (e.g., 8-16) consecutive or approximately consecutive cardiac pressure signal measurements. Alternatively, the height/width ratio can be measured on each of several individual consecutive or approximately consecutive cardiac pressure signal measurements, and a statistical measurement, such as the mean and the variance, can be calculated on the several measurements.

Because during an ischemia, the contractility of cardiac myocytes in the ischemic zone is expected to be compromised, the value of the ratio of the height to the width of the cardiac pressure signal is expected to deviate from a predetermined value (e.g., a previously stored value of the height/width ratio during a non-ischemic period). In one example, the value of the height/width ratio is expected to decrease with respect to the previously stored value of the height/width ratio during a non-ischemic period. Thus, in step 1125, the value of the height/width ratio is compared to a predetermined value. If the value of the ratio has changed from the predetermined value, then an ischemia is indicated in step 1130. Otherwise, monitoring continues and steps 1105-1125 of process 1100 are repeated.

In one example, only one height/width ratio measurement is compared to the predetermined value to indicate an ischemia event. In another example, several consecutive height/width ratio measurements (e.g., three) are compared to the predetermined value before indicating an ischemia event. In yet another example, a rate at which the height/width ratio measurements change with respect to the predetermined value must exceed a threshold (e.g., at least three of five consecutive measurements) before indicating an ischemia event. In a further example, a measure of statistical significance (e.g., T-statistic) relating to the height/width ratio measurement must change with respect to a predetermined value before indicating an ischemia event.

In an embodiment, steps 1110-1130 are implemented using ischemia detector 220 of FIG. 2. As described above, ischemia detector 220 is configured to receive a signal indicative of ventricular cardiac pressure, such as signal 222. During each cardiac cycle, ischemia detector 220 measures a height of cardiac pressure signal 222, such as the height from a baseline value to a peak amplitude of cardiac pressure signal 222, and a width (i.e., duration) of cardiac pressure signal 222. Ischemia detector 220 then determines a ratio of the height to the width. In this example, ischemia detector 220 compares the value of the ratio to a predetermined value, such as a previously stored value of the height/width ratio of cardiac pressure signal 222 during a non-ischemic period, to determine whether to indicate an ischemia.

FIG. 13 shows a process flowchart 1300 providing steps for detecting ischemia using an ICRMD to analyze morphology of a signal indicative of cardiac pressure. In step 1305, a signal indicative of cardiac pressure is acquired. For example, as described above with respect to FIG. 2, physiologic sensor 208 can be configured to acquire ventricular cardiac pressure data via a pressure transducer or other type of sensor and provide an output signal 222 indicative of ventricular cardiac pressure to ischemia detector 220.

In step 1310, during each cardiac cycle, a derivative signal, which is a first derivative of the cardiac pressure signal, is determined.

In step 1315, a maximum positive value of a rising portion of the derivative signal (+dP/dtmax) is measured, and, in step 1320, a maximum negative value of a falling portion of the derivative signal (−dP/dtmax) is measured.

In step 1325 a ratio of the maximum positive value to the maximum negative value (+dP/dtmax/−dP/dtmax) is determined. The +dP/dtmax/−dP/dtmax ratio can be measured on an ensemble-average of several (e.g., 8-16) consecutive or approximately consecutive derivative signal measurements. Alternatively, the +dP/dtmax/−dP/dtmax ratio can be measured on each of several individual consecutive or approximately consecutive derivative signal measurements, and a statistical measurement, such as the mean and the variance, can be calculated on the several measurements.

Because during an ischemia, the contractility of cardiac myocytes in the ischemic zone is expected to be compromised, the value of the +dP/dtmax/−dP/dtmax ratio is expected to deviate from a predetermined value (e.g., a previously stored value of the +dP/dtmax/−dP/dtmax ratio during a non-ischemic period). In one example, the value of the +dP/dtmax/−dP/dtmax ratio is expected to decrease with respect to the previously stored value of the +dP/dtmax/−dP/dtmax ratio during a non-ischemic period. Thus, in step 1330, the value of the +dP/dtmax/−dP/dtmax ratio is compared to a predetermined value. If the value of the ratio has changed from the predetermined value, then an ischemia is indicated in step 1335. Otherwise, monitoring continues and steps 1305-1330 of process 1300 are repeated.

In one example, only one +dP/dtmax/−dP/dtmax ratio measurement is compared to the predetermined value to indicate an ischemia event. In another example, several consecutive +dP/dtmax/−dP/dtmax ratio measurements (e.g., three) are compared to the predetermined value before indicating an ischemia event. In yet another example, a rate at which the +dP/dtmax/−dP/dtmax ratio measurements change with respect to the predetermined value must exceed a second threshold (e.g., at least three of five consecutive measurements) before indicating an ischemia event. In a further example, a measure of statistical significance (e.g., T-statistic) relating to the +dP/dtmax/−dP/dtmax ratio measurement must change with respect to a predetermined value before indicating an ischemia event.

In one embodiment, steps 1310-1335 are implemented using ischemia detector 220 of FIG. 2. As described above, ischemia detector 220 is configured to receive a signal indicative of ventricular cardiac pressure, such as signal 222. During each cardiac cycle, ischemia detector 220 generates a derivative signal, which is a first derivative of cardiac pressure signal 222, and measures a maximum positive value of a rising portion of the derivative signal and a maximum negative value of a falling portion of the derivative signal. Ischemia detector 220 then determines a ratio of the maximum positive value to the maximum negative value. In this example, ischemia detector 220 compares the value of the ratio to a predetermined value, such as a previously stored value of the ratio during a non-ischemic period, to determine whether to indicate an ischemia.

Various forms of the word "measure" are used herein. It will be understood by a person skilled in the art that measuring may involve sensing, detecting, calculating, determining, and/or otherwise ascertaining a value of, for example, a signal amplitude or duration.

CONCLUSION

Example methods and systems for detecting ischemia using an ICRMD have been described herein. As noted elsewhere, these example embodiments have been described for illustrative purposes only, and are not limiting. Other embodiments are possible and are covered by the methods and systems described herein. Such embodiments will be apparent to persons skilled in the relevant art(s) based on the teachings contained herein. Thus, the breadth and scope of the methods and systems described herein should not be limited by any of the above-described exemplary embodiments, but should be defined only in accordance with the following claims and their equivalents.

What is claimed is:

1. A method for detecting ischemia, comprising:
   (a) sensing via an implantable cardiac-rhythm-management device (ICRMD) a signal indicative of cardiac pressure;
   (b) determining via a processor associated with the ICRMD, a derivative signal that is a first derivative of the sensed signal;
   (c) measuring via the processor, a maximum positive value of the derivative signal;
   (d) measuring via the processor, a maximum negative value of the derivative signal; and
   (e) indicating via the processor, an ischemia when a ratio of the maximum positive value to the maximum negative value is less than a previously stored value of the ratio during a non-ischemic event.

2. A method for detecting ischemia, comprising:
   (a) sensing via an implantable cardiac-rhythm-management device (ICRMD) a signal indicative of cardiac pressure;
   (b) determining via a processor associated with the ICRMD, a derivative signal that is a first derivative of the sensed signal;
   (c) measuring via the processor, a maximum positive value of the derivative signal;
   (d) measuring via the processor, a maximum negative value of the derivative signal; and
   (e) indicating via the processor, an ischemia based on a comparison of a ratio of the maximum positive value to the maximum negative value with a predetermined value;
   wherein the derivative signal is an ensemble average of a plurality of separately determined derivative signals.

3. The method of claim 2 wherein:
   steps a) through d) are repeated a plurality of times to obtain a corresponding plurality of ratios of maximum positive value to maximum negative value; and
   step (e) comprises comparing each ratio with the predetermined value and indicating an ischemia when a predetermined number of consecutively obtained ratios deviates from the predetermined value.

4. The method of claim 2 wherein:
   steps a) through d) are repeated a plurality of times to obtain a corresponding plurality of ratios of maximum positive value to maximum negative value; and step (e) comprises comparing each ratio with the predetermined value and indicating an ischemia when a predetermined percentage of consecutively obtained ratios deviates from the predetermined value.

5. A system for detecting ischemia, comprising:
means for sensing a signal indicative of cardiac pressure;
means for determining a derivative signal that is a first derivative of the sensed signal;
means for measuring a maximum positive value of the derivative signal;
means for measuring a maximum negative value of the derivative signal; and
means for indicating an ischemia when a ratio of the maximum positive value to the maximum negative value is less than a previously stored value of the ratio during a non-ischemic event.

6. A system for detecting ischemia, comprising:
a sensor that generates a signal indicative of cardiac pressure; and
an ischemia detector that determines a derivative signal that is a first derivative of the sensed signal; measures a maximum positive value of the derivative signal; measures a maximum negative value of the derivative signal; and indicates an ischemia when a ratio of the maximum positive value to the maximum negative value is less than a previously stored value of the ratio during a non-ischemic event.

\* \* \* \* \*